(12) United States Patent
Dobrinsky

(10) Patent No.: US 10,881,751 B2
(45) Date of Patent: Jan. 5, 2021

(54) ULTRAVIOLET IRRADIATION OF FOOD HANDLING INSTRUMENTS

(71) Applicant: Sensor Electronic Technology, Inc., Columbia, SC (US)

(72) Inventor: Alexander Dobrinsky, Vienna, VA (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 16/369,581

(22) Filed: Mar. 29, 2019

(65) Prior Publication Data

US 2019/0298871 A1 Oct. 3, 2019

Related U.S. Application Data

(60) Provisional application No. 62/651,156, filed on Mar. 31, 2018.

(51) Int. Cl.
*A61L 2/10* (2006.01)
*G01N 21/64* (2006.01)
*G01N 21/94* (2006.01)

(52) U.S. Cl.
CPC ............... *A61L 2/10* (2013.01); *G01N 21/64* (2013.01); *G01N 21/94* (2013.01); *A61L 2202/11* (2013.01); *A61L 2202/14* (2013.01)

(58) Field of Classification Search
CPC .......... A61L 2/08; A61L 2/10; A61L 2202/11; A61L 2202/14; G01N 21/64; G01N 21/94
See application file for complete search history.

(56) References Cited

U.S. PATENT DOCUMENTS

| 3,571,939 | A | * | 3/1971 | Paul ........................ A61L 2/10 34/275 |
| 7,553,456 | B2 | | 6/2009 | Gaska et al. |
| 7,634,996 | B2 | | 12/2009 | Gaska et al. |
| 8,277,734 | B2 | | 10/2012 | Koudymov et al. |
| 8,980,178 | B2 | | 3/2015 | Gaska et al. |
| 9,006,680 | B2 | | 4/2015 | Bettles et al. |
| 9,034,271 | B2 | | 5/2015 | Shur et al. |
| 9,061,082 | B2 | * | 6/2015 | Gaska ........................ A61L 2/10 |
| 9,138,499 | B2 | | 9/2015 | Bettles et al. |

(Continued)

FOREIGN PATENT DOCUMENTS

| GB | 2428382 A * | 1/2007 | ............... A61L 2/10 |
| JP | 201141655 A | 3/2011 | |

*Primary Examiner* — David E Smith
(74) *Attorney, Agent, or Firm* — LaBatt, LLC

(57) ABSTRACT

Ultraviolet irradiation of food handling instruments for purposes of sterilization, disinfection, cleaning and other treatment capabilities. A housing having receptacles receives one or more food handling instruments. Ultraviolet light emitting sources located about the receptacles can direct ultraviolet light towards the receptacles and any food handling instruments placed therein. One or more sensors located about the receptacles can detect operational conditions associated with the receptacles and any food handling instruments received therein. A control unit, operatively coupled to the ultraviolet light emitting sources and the one or more sensors, manages the irradiation of the receptacles and any food handling instruments in the receptacles as a function of the operational conditions detected by the one or more sensors.

20 Claims, 7 Drawing Sheets

(56) References Cited

U.S. PATENT DOCUMENTS

| | | | |
|---|---|---|---|
| 9,179,703 B2 | 11/2015 | Shur et al. | |
| 9,339,570 B2 | 5/2016 | Whitney | |
| 9,572,903 B2 | 2/2017 | Dobrinsky | |
| 9,603,960 B2 | 3/2017 | Dobrinsky et al. | |
| 9,687,577 B2 | 6/2017 | Dobrinsky et al. | |
| 9,707,307 B2 | 7/2017 | Shur et al. | |
| 9,718,706 B2 | 8/2017 | Smetona et al. | |
| 9,724,441 B2 | 8/2017 | Shur et al. | |
| 9,750,830 B2 | 9/2017 | Shur et al. | |
| 9,757,486 B2 | 9/2017 | Dobrinsky et al. | |
| 9,795,699 B2 | 10/2017 | Shur et al. | |
| 9,801,965 B2 | 10/2017 | Bettles et al. | |
| 9,802,840 B2 | 10/2017 | Shturm et al. | |
| 9,878,061 B2 | 1/2018 | Shur et al. | |
| 9,919,068 B2 | 3/2018 | Shur et al. | |
| 9,974,877 B2 | 5/2018 | Bettles et al. | |
| 9,981,051 B2 | 5/2018 | Shur et al. | |
| 9,987,383 B2 | 6/2018 | Bilenko et al. | |
| 9,999,782 B2 | 6/2018 | Shur et al. | |
| 10,004,821 B2 | 6/2018 | Dobrinsky et al. | |
| 10,040,699 B2 | 8/2018 | Smetona et al. | |
| 10,099,944 B2 | 10/2018 | Smetona et al. | |
| 10,166,307 B2 | 1/2019 | Dobrinsky et al. | |
| 2003/0066971 A1* | 4/2003 | Yen | A47J 47/16 250/455.11 |
| 2005/0230639 A1* | 10/2005 | Ancona | A61L 2/10 250/455.11 |
| 2007/0115681 A1* | 5/2007 | Cooper | G01N 21/255 362/555 |
| 2008/0041985 A1* | 2/2008 | Lai | A47J 47/005 241/92 |
| 2009/0110594 A1* | 4/2009 | Shin | A47L 15/4276 422/24 |
| 2011/0155924 A1* | 6/2011 | Lo | A61L 2/10 250/455.11 |
| 2013/0048545 A1 | 2/2013 | Shatalov et al. | |
| 2013/0214174 A1* | 8/2013 | Domenig | G02B 5/0278 250/455.11 |
| 2014/0060104 A1* | 3/2014 | Shur | A61L 2/10 62/264 |
| 2014/0202962 A1 | 7/2014 | Bilenko et al. | |
| 2015/0090903 A1* | 4/2015 | Cole | A61L 2/10 250/492.1 |
| 2016/0106873 A1* | 4/2016 | Dobrinsky | A61L 9/00 250/393 |
| 2016/0128526 A1* | 5/2016 | Dobrinsky | E03D 9/08 4/233 |
| 2017/0057842 A1 | 3/2017 | Dobrinsky et al. | |
| 2017/0100495 A1 | 4/2017 | Shur et al. | |
| 2017/0189711 A1 | 7/2017 | Shur et al. | |
| 2017/0245527 A1 | 8/2017 | Dobrinsky et al. | |
| 2017/0245616 A1 | 8/2017 | Lakios et al. | |
| 2017/0273534 A1* | 9/2017 | Alpert | A61L 2/18 |
| 2017/0281812 A1 | 10/2017 | Dobrinsky et al. | |
| 2017/0290934 A1 | 10/2017 | Dobrinsky et al. | |
| 2017/0360972 A1* | 12/2017 | Huang | H05B 1/0205 |
| 2017/0368215 A1 | 12/2017 | Shatalov et al. | |
| 2018/0028700 A1 | 2/2018 | Dobrinsky et al. | |
| 2018/0092308 A1 | 4/2018 | Dobrinsky et al. | |
| 2018/0104368 A1 | 4/2018 | Dobrinsky et al. | |
| 2018/0117194 A1 | 5/2018 | Dobrinsky et al. | |
| 2018/0185529 A1 | 7/2018 | Shur et al. | |
| 2018/0221521 A1 | 8/2018 | Shur et al. | |
| 2018/0243458 A1 | 8/2018 | Shatalov et al. | |
| 2018/339075 A1 | 11/2018 | Kennedy et al. | |
| 2019/0030477 A1 | 1/2019 | Shatalov | |
| 2019/0098842 A1 | 4/2019 | Estes et al. | |
| 2019/0099613 A1 | 4/2019 | Estes et al. | |
| 2019/0100445 A1 | 4/2019 | Estes et al. | |
| 2019/0100718 A1 | 4/2019 | Estes et al. | |
| 2019/0117811 A1 | 4/2019 | Barber, III | |
| 2019/0125907 A1 | 5/2019 | Dobrinsky | |
| 2019/0135659 A1 | 5/2019 | Smetona et al. | |
| 2019/0201570 A1 | 7/2019 | Dobrinsky et al. | |
| 2019/0231912 A1 | 8/2019 | Dobrinsky et al. | |
| 2019/0263680 A1 | 8/2019 | Dobrinsky | |
| 2019/0299260 A1 | 10/2019 | Shatalov et al. | |
| 2019/0300391 A1 | 10/2019 | Shatalov et al. | |

* cited by examiner

ULTRAVIOLET IRRADIATION OF FOOD HANDLING INSTRUMENTS

REFERENCE TO RELATED APPLICATIONS

The present patent application claims the benefit of U.S. Provisional Application No. 62/651,156, which was filed on 31 Mar. 2018, of which is hereby incorporated by reference.

TECHNICAL FIELD

The disclosure relates generally to ultraviolet irradiation, and more specifically, to a solution for using ultraviolet radiation to irradiate food handling instruments for purposes of sterilization, disinfection, cleaning and other treatment capabilities.

BACKGROUND ART

Knives, kitchen tools, cutting boards and utensils are a few examples of food handling instruments which can come into contact with, and harbor, harmful microorganisms, including bacteria, viruses, and other potential pathogens. These microorganisms can spread such germs from one instrument to another and eventually find its way into food that is prepared by affected instruments. Food with such microorganisms that is ingested can cause serious illness, such as, for example, *salmonella* or an *E coli* infection. Vigilant cleaning of food handling instruments with sufficiently hot water and soap and careful food preparation practices can minimize the risk. However, inconsistent cleaning habits, incorrect water temperature and lax food preparation practices can still contribute to the growth of harmful microorganisms on these food handling instruments.

Moreover, simple cleaning in soap and water is sometimes insufficient to kill all microorganisms on a given surface. Traditional cleaning with water also may be ineffective for items which cannot be completely submerged, such as wood, and items which can trap microorganisms in small spaces, such as knife handles. Other approaches which involve the use of chemicals and extreme heat to clean food handling instruments are somewhat more effective than traditional cleaning with water, but both practices have their disadvantages. For example, heat may damage the food handling instruments or may require a cool-down period before the instruments can be used, while the use of chemicals can often lead to chemical residues left on the instruments that can be harmful if ingested.

SUMMARY OF THE INVENTION

This Summary of the Invention introduces a selection of certain concepts in a brief form that are further described below in the Detailed Description of the Invention. It is not intended to exclusively identify key features or essential features of the claimed subject matter set forth in the Claims, nor is it intended as an aid in determining the scope of the claimed subject matter.

Aspects of the present invention are directed to solutions that use ultraviolet radiation to irradiate food handling instruments for purposes of sterilization, disinfection, and other types of cleaning treatment. The various embodiments implement these solutions in the form of a food handling instrument ultraviolet illuminator that can hold or store a wide variety of food handling instruments and apply ultraviolet radiation to the instruments to effectuate a cleaning treatment of the instruments that can include sterilization, disinfection, and the like. These solutions described with the various food handling instrument ultraviolet illuminators can be realized with other approaches that include, but are not limited to, ultraviolet irradiation systems, devices, tools, apparatuses, mechanisms, etc. Examples of food handling instruments that are suitable for use with any of the food handling instrument ultraviolet illuminators of the various embodiments can include a wide variety of instruments. These food handling instruments can include, but are not limited to, knives, kitchen tools, cutting boards, utensils (e.g., kitchen utensils, food utensils) and fabrics or textiles used in the preparation, cooking, eating and cleaning of food (e.g., towels, potholders, place mats, aprons, etc.). In general, the food handling instrument ultraviolet illuminators are suitable for any food handling instrument that can come into contact with, and harbor, harmful microorganisms, including bacteria, viruses, germs, parasitic agents, pathogens, and other contaminants.

In the various embodiments, ultraviolet light emitting sources can be deployed with the food handling instrument ultraviolet illuminators. Ultraviolet light emitting diodes is one example of ultraviolet light emitting sources that can be utilized. Ultraviolet light emitting diodes offer robust technology which do not utilize high voltages which can be the case with mercury lamps. In addition, ultraviolet light emitting diodes can be easily turned on and off. Also, ultraviolet light emitting diodes do not require quartz enclosures which can be the case with other sources such as mercury lamps. Further, ultraviolet light emitting diodes can be implemented in a variety of arrangements since these ultraviolet light emitting sources can be manufactured as small devices.

The ultraviolet light emitting diodes, like any of the other ultraviolet light emitting sources of the various embodiments, can be configured to operate at peak wavelengths that facilitate sterilization, disinfection, and other types of cleaning treatments of food handling instruments that remove harmful bacteria, viruses, germs, parasitic agents, microorganisms, pathogens, contaminants and the like. In one embodiment, one or more of the ultraviolet light emitting diodes can be configured to generate ultraviolet C (UV-C) radiation at a set of peak wavelengths that range from 230 nm to 280 nm. In one embodiment, one or more of the ultraviolet light emitting diodes can be configured to generate ultraviolet A (UV-A) and/or visible radiation (also referred to as blue-UV radiation) at a set of peak wavelengths that range from 360 nm to 460 nm. In one embodiment, the ultraviolet light emitting diodes can be configured to have some of the ultraviolet light emitting sources generating UV-C radiation and other sources generating blue-UV radiation and ultraviolet B (UV-B) radiation. In one embodiment, the ultraviolet light emitting diodes can differ by at least one of peak wavelength, polar distribution, angular distribution, size, intensity level, orientation or irradiation pattern.

The ultraviolet light emitting sources can be implemented in one of a number of approaches with the food handling instrument ultraviolet illuminators in order to sterilize, disinfect, clean and/or treat food handling instruments. For example, the food handling instrument ultraviolet illuminators can include a housing having a plurality of receptacles each configured to receive one or more food handling instruments. The ultraviolet light emitting sources can be located about the receptacles to direct ultraviolet light towards the receptacles. In one embodiment, the ultraviolet light emitting sources are located within each of the receptacles. For example, the ultraviolet light emitting sources can be placed adjacent to at least one of the inner wall surfaces of the receptacles. In one embodiment, ultraviolet transparent windows can encapsulate the ultraviolet light emitting sources within the inner wall surfaces. To this extent, the ultraviolet transparent windows can separate and provide protection from any food handling instruments inserted in the receptacles, while also transmitting the ultraviolet light from the sources to the instruments. In one embodiment, the ultraviolet light emitting sources can have a modular design such that the sources are removably attachable with the housing (e.g., insertable and removable from the receptacles). In this manner, the ultraviolet light emitting sources can be removed from the housing for repair, maintenance, and replacement. In one embodiment, the ultraviolet light emitting sources can be located over the receptacles. To this extent, the ultraviolet light emitting sources are oriented to direct ultraviolet light downward towards the receptacles and surfaces that are in proximity to the receptacles.

A control unit can be operatively coupled to the ultraviolet light emitting sources to control the irradiation of the food handling instruments. For example, the control unit can manage the irradiation of the receptacles and any food handling instruments in the receptacles as a function of operational conditions detected by one or more sensors that can be deployed about the housing. In one embodiment, the control unit can control the intensity, and the duration of the irradiation as a function of time that the food handling instruments are held or stored in the receptacles. In addition to controlling the intensity, and the duration of the irradiation by the ultraviolet light emitting sources, the control unit can control other irradiation parameters including, but not limited to, the wavelength of the ultraviolet radiation emitted by the sources, the overall dosage of the ultraviolet radiation delivered by the sources, the power setting for operating the sources, and the maximum operating temperature of the sources.

The control unit can include a number of different components that can enable it to control the ultraviolet light emitting sources. For example, other components that may be utilized with the control unit can include a timer, an input component and an output component. The timer can be utilized in a number of different manners. For example, the timer can be configured to specify treatment times for operating the ultraviolet light emitting sources in order to ensure that the sources deliver a sufficient dosage to the food handling instruments. The timer can also be used to record the amount of time that food handling instruments reside in the receptacles per data obtained by presence sensors and processed by the control unit. In this manner, the control unit can direct the ultraviolet light emitting sources to irradiate food handling instruments that have been in a receptacle over a predetermined time (e.g., a time period that is associated with an incipient rise in contaminant levels about the surfaces of food handling instruments). For example, the control unit can begin an irradiation treatment of the instrument(s) by activating a set of UV-C light emitting sources after the timer measures that a food handling instrument has resided in a receptacle for at least the predetermined time.

The input component and the output component, which can take the form of a user input/output component, can facilitate user interaction with the control unit to control the irradiation of the food handling instruments in the receptacles with the ultraviolet light emitting sources. For example, the user input/output component can receive user input that adjusts one or more irradiation parameters associated with the ultraviolet light emitting sources. The user input/output component can also be configured to generate information indicative of the irradiation of the food handling instruments in the receptacles by the ultraviolet light emitting sources. The information can include, but are not limited to, at least one of displaying an indication that the ultraviolet light emitting sources are irradiating food handling instruments in a receptacle, displaying an indication of one or more irradiation parameters (e.g., radiative dose delivered to food handling instruments) associated with the sources, or displaying an indication of a date of the most recent irradiation treatment by the ultraviolet light emitting sources. The timer and the user input/output components can be integrated with the control unit they can be implemented to operate in conjunction with the control unit, the ultraviolet light emitting sources and other components (e.g., sensors, other sources).

In one embodiment, the food handling instrument ultraviolet illuminators of the various embodiments can include at least one sensor configured to detect operational conditions associated with the plurality of receptacles and any food handling instruments received therein. A number of different sensors can be used singly or in a multiple of combinations to detect operational conditions of the receptacles and any food handling instruments placed therein, including conditions of these item during irradiation. The sensors, which can include more than one of each type, can comprise, but are not limited to, a fluorescent sensor to detect the fluorescence emissivity generated from the surface of a food handling instrument after irradiation by one or more of the ultraviolet light emitting sources and a presence sensor to detect the presence of a food handling instrument in a receptacle upon placement therein. Other sensors can include a temperature sensor to detect the temperature about the receptacles, a humidity sensor to detect the humidity about the receptacles including the food handling instruments stored in the receptacles, an ultraviolet radiation sensor to detect the ultraviolet intensity within the receptacles and at the surfaces of the food handling instruments placed in the receptacles, a visible sensor such as a visible camera that can obtain images from surfaces of the food handling instrument(s) placed in a corresponding receptacle, a proximity sensor that is configured to detect the presence of a moving body that comes within the vicinity of the plurality of ultraviolet light emitting sources and/or the plurality of receptacles, and any of a number of environmental sensors that can detect environmental conditions (e.g., a presence of contaminants).

The control unit can obtain data from any of the sensors and use this data to control the irradiation of the receptacles and any instruments placed therein. In this manner, the ultraviolet light emitting sources, the control unit and the sensors provide the various embodiments with a feedback mechanism that facilitates monitoring the irradiation of the receptacles and the instruments. For example, this feedback mechanism enables the control unit to determine a presence of harmful contaminants about the receptacles and the surfaces of the food handling instruments based on the conditions detected by the sensor(s). This allows the control unit to direct the ultraviolet light emitting sources to irradiate the receptacles and the surfaces of the food handling instruments at locations where there is a presence of harmful contaminants for removal and suppression thereof.

In one embodiment, the control unit can determine whether the intensity of the fluorescent signal detected by the fluorescent sensor is indicative of a contamination condition present on the surface of a food handling instrument in a receptacle. In this manner, the control unit can activate the ultraviolet light emitting sources to perform a disinfection operation on the instrument in response to determining the contamination condition. In one scenario, the ultraviolet light emitting sources can direct a set of blue ultraviolet light emitting sources and/or UV-C light emitting sources to perform the disinfection operation. For example, the control unit can direct the set of blue ultraviolet light emitting sources to continuously radiate a food handling instrument in a receptacle for a predetermined prolonged period of time to inhibit biological growth and the set of UV-C light emitting sources to radiate the instrument in a pulsed regime to reduce biological activity below a target level.

In addition, the control unit can be used to monitor the irradiation of the receptacles and any food handling instruments therein with feedback from the conditions detected by any of the sensors. To this extent, the control unit can adjust any of the aforementioned irradiation parameters of the ultraviolet light emitting sources as a function of conditions detected by the sensors. For example, a fluorescent sensor can be configured to detect the intensity, the dosage, and the wavelength of the ultraviolet light that irradiates the food handling instruments. To this extent, the fluorescent sensor can provide this data to the control unit which can use the data to determine whether the irradiation is sufficient to perform the desired treatment of the instruments. If necessary, the control unit can adjust the irradiation parameters of the ultraviolet light emitting sources accordingly to ensure that the desired treatment is attained.

In one embodiment, the control unit can operate in conjunction with an ultraviolet radiation sensor and a fluorescent sensor. For example, an ultraviolet radiation sensor can be configured to detect the ultraviolet intensity that is in proximity of a food handling instrument in a receptacle after being irradiated with ultraviolet radiation from the ultraviolet light emitting sources. The control unit can be configured to adjust the intensity of the ultraviolet light emitting sources irradiating the receptacles and food handling instruments placed therein as a function of the intensity detected by the ultraviolet radiation sensor. In one embodiment, an ultraviolet radiation sensor can be configured to detect the ultraviolet intensity that is in proximity of a food handling instrument in a receptacle after being irradiated with ultraviolet from a first set of ultraviolet light emitting sources, while a fluorescent sensor can be configured to detect the fluorescent illumination intensity excited from a surface of the food handling instrument after being irradiated by a second set of ultraviolet light emitting sources. In this manner, the control unit can receive signals indicative of the conditions detected by the ultraviolet radiation sensor and the fluorescent sensor, and determine a density level of a target contaminant that is present on a surface of the food handling instrument. In this manner, the control unit can activate one or more the ultraviolet light emitting sources to direct ultraviolet light towards the surface of the food handling instrument to eradicate the target contaminant in response to determining that the contaminant density level satisfies a predetermined threshold.

In one embodiment, the control unit can operate in conjunction with a visible camera that is configured to obtain images from surfaces of food handling instruments placed in a receptacle. In particular, the control unit can determine a presence of contamination on the surfaces of the food handling instruments by comparing images obtained by the visible cameras over different times. The control unit can then direct the ultraviolet light emitting sources to irradiate the food handling instruments where there is a presence of contamination for removal thereof and suppression of further growth. In addition, the control unit can monitor the irradiation of the food handling instruments with the visible camera, and adjust irradiation parameters of the ultraviolet light emitting sources as a function of conditions detected by the visible camera.

In one embodiment, a fluorescent sensor can operate in conjunction with a visible camera to effectuate an irradiation treatment. For example, the fluorescent sensor can detect the fluorescent illumination intensity excited from a surface of the food handling instruments after being irradiated by the ultraviolet light emitting sources and the visible camera can obtain images of the fluorescent response generated from the surface of the food handling instruments.

The control unit can determine a presence of contamination on the surfaces of the food handling instruments by comparing images of the fluorescent responses obtained by the visible camera over different times. In this manner, the control unit can be configured to direct the ultraviolet light emitting sources to irradiate the food handling instrument in response to determining a presence of contamination. The control unit can also be configured to monitor the irradiation of the food handling instruments with the visible camera, and adjust irradiation parameters of the ultraviolet light emitting sources as a function of fluorescent responses detected by the visible camera.

The food handling instrument ultraviolet illuminator of the various embodiments can be configured with one of a number of optical elements that can facilitate the irradiation of food handling instruments in the receptacles for purposes of sterilization, disinfection, cleaning and/or treating surfaces of the instruments for eradicating harmful bacteria, viruses, germs, parasitic agents, microorganisms, pathogens, contaminants, and the like. In one embodiment, at least one optical element can be deployed to distribute the ultraviolet light emitted from the ultraviolet light emitting sources about the surfaces of the food handling instruments. For example, the optical element can include at least one of a mirror, a reflector, a lens (e.g., a Fresnel lens and a total internal reflection (TIR) lens), ultraviolet transparent wave guiding material, scattering elements, or a diffusive element.

In one embodiment, a light guiding layer can be optically coupled to the ultraviolet light emitting sources to guide the ultraviolet light in a predetermined pattern that optimizes the type of treatment that is applied to the food handling instruments. In a scenario in which the ultraviolet light emitting sources are located on the inner wall surfaces of the receptacles, the light guiding layer can be placed about the sources to guide or propagate light through a region of the layer before irradiating the instruments. In one embodiment, the light guiding layer can include one or more ultraviolet transparent layers. The ultraviolet transparent layers can have at least one of roughness domains or diffusive domains that allow extraction of the ultraviolet light from the light guiding layer to the surfaces of the food handling instruments. In one embodiment, the ultraviolet transparent layers can include glass. In one embodiment, the light guiding layer can have scattering elements that interact with the ultraviolet light propagating through the layer and redirect it to the surfaces of the food handling instruments.

In one embodiment, the food handling instrument ultraviolet illuminators can utilize a reflective layer to reflect the ultraviolet light generated from the ultraviolet light emitting sources. For example, the inner wall surfaces of the receptacles can have at least one reflective layer to reflect the ultraviolet light generated from the ultraviolet light emitting sources specularly or diffusively. The at least one reflective layer can include a fluoropolymer layer or an aluminum layer. In one embodiment, the at least one reflective layer can include UV-A or UV-C reflective material.

The aforementioned optical elements can be arranged about the food handling instrument ultraviolet illuminators in any of a number of configurations. For example, these optical elements can be disposed about the receptacles in a number of locations that include, but are not limited to, on an inner wall of the receptacles, on an external wall of the housing, or suspended above the housing and its receptacles.

The food handling instrument ultraviolet illuminators can be formed of materials that can facilitate the irradiation of the food handling instruments for purposes of sterilization, disinfection, cleaning, and/or treating its surfaces for removing harmful bacteria, viruses, germs, parasitic agents, microorganisms, pathogens, contaminants, and the like. For example, the receptacles of the housing can include inner wall surfaces that have a bio-resistance to bacterial growth and are chemically inert to ultraviolet light. In one embodiment, the inner wall surfaces of the receptacles and the housing can include an ultraviolet absorbing, non ultraviolet degrading material. The inner wall surfaces of the receptacles can also have ultraviolet transparent material that emits ultraviolet light from the ultraviolet light emitting sources while preventing humidity from penetrating and damaging the sources.

The food handling instrument ultraviolet illuminator of the various embodiments can be further configured with other components that complement the irradiation of the receptacles and food handling instruments placed therein in order to further enhance the sterilization, disinfection, cleaning and/or treatment. For example, the irradiation of the food handling instruments can also be enhanced by using other sources in addition to the ultraviolet light emitting sources. In particular, at least one visible light emitting source can be used to emit visible light towards the receptacles and any food handling instruments placed therein. In one embodiment, at least one fluorescent radiation source can be used to emit fluorescent radiation towards the food handling instruments. To this extent, the fluorescent radiation source can aid the ultraviolet light emitting sources in disinfecting any harmful contaminants from the surfaces of the food handling instruments and suppressing further growth. In one embodiment, a heating and air circulation unit can be positioned about the receptacles, to direct heated air towards the receptacles and any food handling instruments placed therein.

In one embodiment, a photocatalyst material can be used with any of the various embodiments to facilitate the irradiation of the food handling instruments. For example, the photocatalyst material can include an ultraviolet active photocatalyst located on an inner wall surface of each of the receptacles. The ultraviolet active photocatalyst is configured to undergo a photocatalytic reaction in response to being irradiated by ultraviolet light. The photocatalytic reaction facilitates removal and suppression of any harmful contaminants present on the inner wall surfaces of the receptacles and/or any food handling instruments placed therein. In one embodiment, the photocatalytic reaction can include forming reactive oxygen species (ROS) that interact and disrupt the proliferation of the harmful contaminants.

The food handling instrument ultraviolet illuminators of the various embodiments described herein can have a power component that supplies power to the ultraviolet light emitting sources, the sensor(s), the control unit and any other components (e.g., the timer, the user input/output component). In one embodiment, the power component can include a power station that is removably attachable with the housing. For example, the power station can include an insertable electrical contact that is removably attachable with a bottom portion of the housing. In one embodiment, the power component can be integrated about the housing.

A first aspect of the invention provides a food handling instrument ultraviolet illuminator, comprising: a housing having a plurality of receptacles each configured to receive one or more food handling instruments; a plurality of ultraviolet light emitting sources located about the plurality of receptacles to direct ultraviolet light towards the receptacles; one or more sensors located about the plurality of receptacles to detect operational conditions associated with the plurality of receptacles and any food handling instruments received therein; and a control unit, operatively coupled to the plurality of ultraviolet light emitting sources and the one or more sensors, wherein the control unit is configured to manage the irradiation of the plurality of receptacles and any food handling instruments in the receptacles with the plurality of ultraviolet light emitting sources as a function of the operational conditions detected by the one or more sensors.

A second aspect of the invention provides a food handling instrument ultraviolet illuminator, comprising: a housing having a plurality of receptacles each configured to receive one or more food handling instruments; a plurality of ultraviolet light emitting sources located within each of the plurality of receptacles to direct ultraviolet light towards any food handling instruments placed within the receptacles, wherein the plurality of ultraviolet light emitting sources direct the ultraviolet light to multiple surfaces of the food handling instruments including front and back surfaces of the food handling instruments, wherein at least one of the plurality of ultraviolet light emitting sources is an ultraviolet-C (UV-C) light emitting source configured to irradiate the surfaces of the food handling instrument with a peak wavelength in an ultraviolet-C (UV-C) disinfection range of 230 nm to 280 nm; one or more sensors located about the plurality of receptacles to detect operational conditions associated with the plurality of receptacles and any food handling instruments received therein; and a control unit, operatively coupled to the plurality of ultraviolet light emitting sources and the one or more sensors, wherein the control unit is configured to manage the irradiation of any food handling instruments in the receptacles with the plurality of ultraviolet light emitting sources as a function of the operational conditions detected by the one or more sensors.

A third aspect of the invention provides a food handling instrument ultraviolet illuminator, comprising: a housing having a plurality of compartments each configured to receive one or more food handling instruments that vary by at least one of size, shape or function, wherein the compartments vary by at least one of size, shape, or depth within the housing; a plurality of ultraviolet light emitting sources located within each of the plurality of compartments to direct ultraviolet light towards any food handling instruments placed in the compartments, wherein at least one of the plurality of ultraviolet light emitting sources is an ultraviolet-C (UV-C) light emitting source configured to irradiate the surfaces of the food handling instruments with a peak wavelength in an ultraviolet-C (UV-C) disinfection of 230 nm to 280 nm; one or more sensors located about the plurality of compartments to detect contamination levels on any food handling instruments received therein; a control unit, operatively coupled to the plurality of ultraviolet light emitting sources and the one or more sensors, wherein the control unit is configured to direct the plurality of ultraviolet light emitting sources to irradiate surfaces of any food handling instruments deemed to have contamination levels satisfying a predetermined contamination level, wherein the control unit is configured to monitor the irradiation of the food handling instruments and adjust the intensity of any of the ultraviolet light emitting sources as a function of the contamination levels detected by the one or more sensors; and a user input/output component configured to facilitate user interaction with the control unit to control the irradiation of the food handling instruments by the plurality of ultraviolet light emitting sources.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
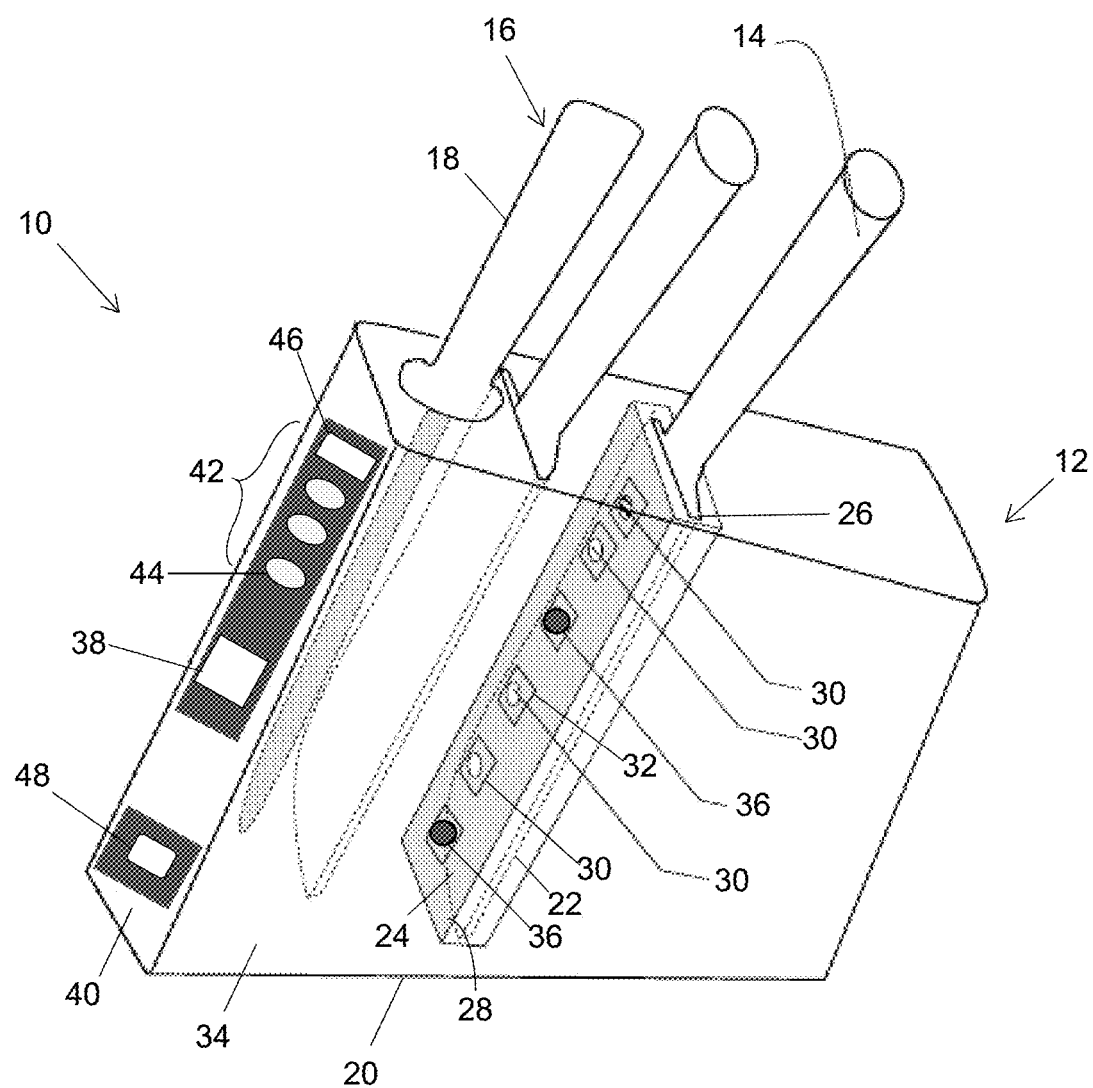
FIG. 1 shows a schematic of a food handling instrument ultraviolet illuminator for irradiating a knife set and accompanying implements according to an embodiment.

Aspects of the invention are directed to solutions that use ultraviolet radiation to irradiate food handling instruments for purposes of sterilization, disinfection, cleaning and/or treating of microorganisms, parasitic agents, bacteria, viruses, germs or other harmful contaminants. Sanitizing generally means reducing the number of bacterial contaminants to a predetermined safe level. Disinfecting generally means destroying pathogenic and other types of microorganisms, while sterilizing can be more extensive in that it kills all microbial forms and/or includes destroying the ability of the microbial forms to reproduce. Cleaning and/or treating, which can be used interchangeably, generally means any actions, steps and the like that effectuate at least one of sanitizing, disinfecting or sterilizing.

Ultraviolet radiation, which can be used interchangeably with ultraviolet light, means electromagnetic radiation generally described as having a wavelength ranging from approximately 10 nm to approximately 400 nm. Within this range, there is ultraviolet-A (UV-A) electromagnetic radiation generally described as having a wavelength ranging from approximately 315 nm to approximately 400 nm, ultraviolet-B (UV-B) electromagnetic radiation generally described as having a wavelength ranging from approximately 280 nm to approximately 315 nm, and ultraviolet-C (UV-C) electromagnetic radiation generally described as having a wavelength ranging from approximately 100 nm to approximately 280 nm. It is understood that a light emitting source configured to operate in a particular range can emit ultraviolet radiation in an adjacent range. For example, as used herein, a UV-C source can also emit UV-B radiation, e.g., 280 nm to 290 nm. As used herein, blue-UV radiation includes at least a portion of the UV-A electromagnetic radiation as well as higher wavelength visible light, e.g., visible light having a wavelength ranging from approximately 400 nm to approximately 460 nm (360 nm to 460 nm in a more particular embodiment).

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 nm to about 290 nm provides the highest germicidal effectiveness, while an ultraviolet radiation between about 260 nm to about 310 nm is sufficient for providing overall germicidal effectiveness, and ultraviolet radiation between 250 nm to 280 nm is a range for facilitating sterilization and disinfection of a vast amount of objects and fluids that can develop the presence of contaminants. While susceptibility to ultraviolet radiation varies, exposure to ultraviolet energy in the above range for about 20 to about 34 milliwatt-seconds/cm$^2$ is adequate to deactivate approximately 99 percent of the pathogens.

As used herein, a material/structure/layer is considered to be "reflective" to ultraviolet light of a particular wavelength when the material/structure/layer has an ultraviolet reflection coefficient of at least 30 percent for the ultraviolet light of the particular wavelength. A highly ultraviolet reflective material/structure/layer has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through.

The food handling instrument ultraviolet illuminators as described in the various embodiments can include a number of components. These components are described below in more detail, some of which may be optional, facilitate treatment of one or more food handling instruments. The modalities used with the various food handling instrument ultraviolet illuminators described herein including its respective components can include any now known or later developed approaches that incorporate the concepts of the embodiments described below in more detail.

The description that follows may use other terminology herein for the purpose of only describing particular embodiments and is not intended to be limiting of the disclosure. For example, unless otherwise noted, the term "set" means one or more (i.e., at least one) and the phrase "any solution" means any now known or later developed solution. The singular forms "a," "an," and "the" include the plural forms as well, unless the context clearly indicates otherwise. It is further understood that the terms "comprises," "comprising," "includes," "including," "has," "have," and "having" when used in this specification, specify the presence of stated features, integers, steps, operations, elements, and/or components, but do not preclude the presence or addition of one or more other features, integers, steps, operations, elements, components, and/or groups thereof. Additionally, spatially relative terms, such as "on," "below," "above," etc., may be used in reference to the orientation shown in the drawings. It is understood that embodiments of the invention are not limited to any particular orientation of a device described herein. Also, the use of a phrase of the form "at least one of A, B, C . . . or n" to delineate a listing of two or more possible parameters, components, characteristics, factors, etc., means any combination of one or more of A, B, C, . . . n. For example, at least one of A or B means only A, only B, or both A and B.

The description may also list values of parameters of elements, components, objects, materials, layers, structures, and the like, for the purpose of describing further details of particular embodiments. It is understood that, unless otherwise specified, each value is approximate and each range of values included herein is inclusive of the end values defining the range. As used herein, unless otherwise noted, the term "approximately" is inclusive of values within +/−ten percent of the stated value, while the term "substantially" is inclusive of values within +/−five percent of the stated value. Unless otherwise stated, two values are "similar" when the smaller value is within +/−twenty-five percent of the larger value. A value, y, is on the order of a stated value, x, when the value y satisfies the formula $0.1x \leq y \leq 10x$. Unless otherwise stated, as used herein, parameters can have comparable values when the values of the corresponding parameters differ by at most ten percent (five percent in a more specific embodiment).

Turning to the drawings, FIG. 1 shows a schematic of a food handling instrument ultraviolet illuminator 10 in the form of a food handling instrument block 12 that can hold a set of knives 14 and accompanying implements 16 and irradiate the knives and implements while they are stored therein. The food handling instrument block 12 can hold and store various types and sizes of knives 14 and implements 16. For example, the implements 16 can include, but are not limited to a honing steel 18 (e.g., a sharpening stick or rod), scissors, spatulas, spoons, forks and other cutlery items.

The food handling instrument ultraviolet illuminator 10 can include a housing 20 or enclosure having a plurality of receptacles 22 each configured to receive one or more food handling instruments such as the knives 14 and the implements 16. In one embodiment, each of the receptacles 22 includes a storage chamber 24 formed in an opening 26 that extends into the housing with inner wall surfaces 28 surrounding the storage chamber. The size and shape of the receptacles 22 can vary in order to receive correspondingly sized and shaped food handling instruments that can also differ in function. In addition, the depth that the receptacles 22 extend into the housing 20 can vary in order to accommodate different sized and shaped food handling instruments. It is understood that the number of receptacles 22 and the food handling instruments placed in these receptacles as depicted in FIG. 1 is only illustrative, and not meant to be limiting. Similarly, the type of food handling instruments that can be placed in the receptacles 22 is not meant to be limited to knives 14 and a honing steel 18, but can include other types of cutlery.

The food handling instrument ultraviolet illuminator 10 can include a plurality of ultraviolet light emitting sources 30 located about the plurality of receptacles 22 to direct ultraviolet light towards the receptacles for purposes of sterilization, disinfection, cleaning and/or treating surfaces of any food handling instruments placed therein. To this extent, the ultraviolet light generated from the ultraviolet light emitting sources 30 can be used to eradicate harmful bacteria, viruses, germs, parasitic agents, microorganisms, pathogens, contaminants and the like from the food handling instruments and even surfaces about the receptacles including, but not limited to, the storage chambers 24, the openings 26, and the inner wall surfaces 28 of the receptacles 22.

As used herein, "located about the receptacles" means locations that can include on interior or exterior wall surfaces of the receptacles 22 and the housing 20 or within a predetermined distance away from these items that is capable of delivering radiation to the food handling instruments that is effective for treating the instruments. In one embodiment, as depicted in FIG. 1, the ultraviolet light emitting sources 30 can be located within each of the receptacles 22. For example, the ultraviolet light emitting sources 30 can be placed adjacent to at least one of the inner wall surfaces 28 that surrounds the storage chamber 24. In one embodiment, the ultraviolet light emitting sources 30 located within each of the receptacles 22 can take the form of a module of sources that are removably attachable with the receptacles. In one embodiment, the module can include an ultraviolet transparent window formed over the sources such that the window is placed between the storage chamber of the receptacles and the sources. In one embodiment, the receptacles 22 can contain rollers and/or holders to secure the food handling instruments (e.g., the blades of the knives) at a predetermined distance from the inner wall surfaces of the receptacles to ensure consistent exposure of the instruments (e.g., the blades of the knives) to radiation.

The ultraviolet light emitting sources 30 can comprise any combination of one or more ultraviolet radiation emitter. For example, the set of ultraviolet light emitting sources 30 can include a high intensity ultraviolet lamp (e.g., a high intensity mercury lamp), a discharge lamp, ultraviolet light emitting diodes (LEDs), deep ultraviolet LEDS, super luminescent LEDs, laser diodes, and/or the like. In an embodiment, the ultraviolet light emitting sources can include a set of light emitting diodes manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). Additionally, the set of ultraviolet light emitting sources 30 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a wave guide, a plurality of ultraviolet fibers, each of which terminates at an opening, a diffuser, and/or the like. In addition, optical elements including but not limited to, lenses, prismatic ultraviolet transparent elements, mirror elements (e.g., a parabolic mirror element, an omnidirectional mirror, a planar mirror and/or the like) can be deployed as primary and/or secondary optical elements for focusing the radiation in a particular pattern and/or direction from the sources.

The ultraviolet light emitting sources 30 can be configured to operate at peak wavelengths that facilitate sterilization, disinfection, cleaning and/or treatment of the food handling instruments in the receptacles 22 that remove harmful bacteria, viruses, germs, parasitic agents, microorganisms, pathogens, contaminants and the like from the surfaces of the instruments. In one embodiment, the ultraviolet light emitting sources 30 can differ by at least one of peak wavelength, polar distribution, angular distribution, size, intensity level, dosage, orientation or irradiation pattern in order to facilitate efficient irradiation and/or higher disinfection rates of the food handling instruments. The use of the ultraviolet light emitting sources 30 can have significant effects on the sterilization, disinfection, cleaning and/or treatment of the food handling instruments such as the knives 14. For example, the use of the ultraviolet light emitting sources 30 to irradiate the food handling instruments can provide a reduction of microorganism (e.g., bacterial and/or viral) contamination on their surfaces by at least a factor of two. In one embodiment, the food handling instrument ultraviolet illuminator of the various embodiments through the use of the ultraviolet light emitting sources 30 and other components (e.g., a control unit and sensors) mentioned below can provide approximately 99.9% decontamination of the food handling instruments.

In one embodiment, the ultraviolet light emitting sources 30 can include a first set of ultraviolet light emitting sources configured to operate at a blue ultraviolet wavelength ranging from 360 nm to 460 nm, a second set of ultraviolet light emitting sources configured to operate at an ultraviolet-C (UV-C) wavelength ranging from 260 nm to 290 nm. In a specific embodiment, the ultraviolet light emitting sources (i.e., UV-C light emitting sources) can operate at an UV-C wavelength ranging from 230 nm to 280 nm. In another embodiment that provides efficient inactivation of bacterial contaminations, the first set of ultraviolet light emitting sources can operate at a blue ultraviolet wavelength ranging from 360 nm to 430 nm, while the second set of ultraviolet light emitting sources can operate at a UV-C wavelength ranging from 260 nm to 290 nm. In another embodiment, the ultraviolet light emitting sources 30 can include a first set of ultraviolet light emitting sources operating at an UV-C wavelength, a second set of ultraviolet light emitting sources operating at a blue ultraviolet wavelength, and a third set of ultraviolet light emitting sources operating at an UV-B wavelength.

In general, the blue-UV light emitting sources comprise high intensity wide coverage sources that are capable of continuous operation in an efficient matter over a large stretch of time (e.g., several days), while the UV-C light emitting sources can operate at specific wavelengths optimized to treat certain microorganisms, pathogens, viruses, parasitic agents, and the like. Irradiating the food handling instruments with multiple wavelengths of radiation that is afforded with the use of the blue ultraviolet light emitting sources and the UV-C light emitting sources enables the ultraviolet light emitting sources 30 to deliver a variety of irradiation treatments. For example, the blue ultraviolet light emitting sources can deliver blue-UV radiation to the food handling instrument over a prolonged period of time that can range from tens of minutes to tens of hours, while the UV-C light emitting sources can emit UV-C radiation to perform a more intense ultraviolet irradiation treatment at a short burst of intensity that lasts at most a few minutes. In this manner, the UV-C radiation can rapidly bring any microbial activity on the food handling instrument to within appropriate limits, while the blue-UV radiation can maintain microbial activity within limits over an extended period of time.

It is understood that both UV-C, blue-UV, and UV-B light emitting sources are capable of producing a distributed intensity over an area of the food handling instruments in the receptacles 22 at a certain distance from the sources, where distances can range from a few centimeters to several meters. As used herein, irradiation of a location defines a region that is impinged by radiation, wherein the intensity of radiation deposited at the boundary of the region is at most 10% of the intensity of light deposited at the center of the region. It is understood that the position of irradiated locations can be adjusted to result in separate locations, wherein "separate" means that the intensity of radiation between the locations is no larger than 10% of the intensity in the center of the locations. In addition, these locations of irradiation can be designed to have relatively uniform radiation, with radiation intensity varying through the volume or location of no more than several times between any two points within the volume or location.

In one embodiment, an ultraviolet transparent window 32 can be formed on the inner wall surfaces 28 of the receptacles 22 over the ultraviolet light emitting sources 30 to facilitate transmissivity of the light generated from the sources. The ultraviolet transparent windows 32 can be formed from one of a variety of materials. For example, the ultraviolet transparent windows 32 can comprise an ultraviolet transparent fluoropolymer that can transmit ultraviolet light. In one embodiment, ultraviolet transparent fluoropolymers that can be used for the ultraviolet transparent windows 32 can include a terpolymer of ethyelene, tetrafluoroethylene, and hexafluoropropylene (EFEP), an amorphous fluoropolymer (e.g., Cytop®), polytetrafluoroethylene (e.g., Teflon®), and/or the like. In an alternative embodiment, an ultraviolet transparent window 32 can comprise $SiO_2$, $SiO_2$ derivatives such as moldable silicone, $Al_2O_3$, $CaF_2$, $MgF_2$, and/or the like. It is understood that other ultraviolet transparent materials can be used to form the ultraviolet transparent windows 32.

In one embodiment, as shown in FIG. 1, the ultraviolet transparent window 32 can include distinct ultraviolet transparent windows that correspond to the type of ultraviolet light emitting sources that each operates in conjunction with. For instance, distinct ultraviolet transparent windows can be formed over each blue ultraviolet light emitting source and each UV-C light emitting source. In one embodiment, the ultraviolet transparent windows formed over the blue ultraviolet light emitting sources can include a different material than the ultraviolet transparent windows formed over the UV-C light emitting sources. Although FIG. 1 depicts the use of a plurality of distinct windows 32, it is understood that a single ultraviolet transparent window can be formed along the inner wall surfaces 28 to cover all of the ultraviolet light emitting sources 30 used with a receptacle 22.

It is understood that the ultraviolet light emitting sources 30 can be positioned about the inner wall surfaces 28 of the receptacles in configurations that differ from those depicted in FIG. 1, but still with the capability to irradiate a lateral area of any object inserted into the receptacles. For example, the ultraviolet light emitting sources 30 can positioned on only a limited range of the inner wall surfaces 28 (e.g., in a central position). In addition, the ultraviolet light emitting sources 30 can be located on opposing inner wall surfaces 28 in order to irradiate multiple side surfaces of a food handling instrument placed in a receptacle 22. In general, it is understood that the arrangement possibilities of the ultraviolet light emitting sources 30 is extensive and thus, the embodiment depicted in FIG. 1 as well as other embodiments described herein are not meant to be limited to any one specific configuration. Similarly, the number of ultraviolet light emitting sources 30 at one location can vary, and any number of sources or other components that are depicted in the figures are not meant to be limiting to any of the embodiments described herein.

In addition to being located at multiple locations, the ultraviolet light emitting sources 30 can be movable, such that the sources can be moved and oriented to direct ultraviolet radiation in a desired manner to effectuate a particular treatment of the food handling instruments. For example, the ultraviolet light emitting sources 30 can be configured to be moveable over a predetermined number of degrees of freedom to facilitate irradiation of desired locations about the food handling instruments. In one embodiment, the ultraviolet light emitting sources 30 can be placed in the bottom location of the storage chamber 24 of the receptacles 22 in an orientation that is pointing directly upwards, or slightly tilted to irradiate the sides or inner wall surfaces 28 and any food handling instruments placed therein.

The food handling instrument ultraviolet illuminator 10 can be formed of materials that facilitate the irradiation of food handling instruments for purposes of sterilization, disinfection, cleaning, and/or treating their surfaces for removing harmful bacteria, viruses, germs, parasitic agents, microorganisms, pathogens, contaminants, and the like. For example, the inner wall surfaces 28 can have a bio-resistance to bacterial growth and are chemically inert to ultraviolet light. In one embodiment, the exterior wall surfaces 34 of the housing 20 can include an ultraviolet absorbing, non ultraviolet degrading material that prevents radiation from escaping outside the housing.

In embodiments in which the ultraviolet light emitting sources 30 are located on the inner wall surfaces 28 of the receptacles 22, the sources can be encapsulated to protect these components from environmental factors such as humidity. For example, an ultraviolet transparent material can be used to encapsulate the sources while preventing humidity from penetrating and damaging the sources. In one embodiment, the ultraviolet transparent material can include an ultraviolet transparent fluoropolymer that encapsulates the ultraviolet light emitting sources 30. Ultraviolet transparent fluoropolymers that include, but are not limited to, fluorinated ethylene propylene (FEP), tetrafluoroethylene hexafluoropropylene vinylidene fluoride (THV), polytetrafluoroethylene (PTFE), an amorphous fluoropolymer (e.g., Cytop® by Bellex International Corporation), and/or the like, are examples of ultraviolet transparent material that are suitable for encapsulating and protecting the ultraviolet light emitting sources 30 while allowing the transmission of the light for irradiation purposes.

In one embodiment, the ultraviolet transparent material can comprise an ultraviolet transparent film. For example, the ultraviolet transparent film can cover at least one light emitting side of the ultraviolet light emitting sources 30. However, it is understood that the ultraviolet transparent film can be formed at other locations about the ultraviolet light emitting sources. For example, the ultraviolet transparent film can be adjacent ultraviolet light emitting sources that are configured to emit radiation through a corresponding ultraviolet transparent window to facilitate transmissivity of any light that does not pass through the windows. In one scenario in which the ultraviolet light emitting sources 30 include an ultraviolet light emitting diode die, the ultraviolet transparent film can be placed adjacent to the surface of the die. The ultraviolet transparent film can comprise a thin fluoropolymer film including, but not limited to, a terpolymer of ethyelene, tetrafluoroethylene, and hexafluoropropylene (EFEP), an amorphous fluoropolymer (e.g., Cytop®), polytetrafluoroethylene (e.g., Teflon®), and/or the like. In an alternative embodiment such elements can comprise $SiO_2$, $Al_2O_3$, $CaF_2$, $MgF_2$, and/or the like.

The food handling instrument ultraviolet illuminator of the various embodiments can include one or more sensors 36 located about the receptacles 22 to detect operational conditions associated with the receptacles and any food handling instruments received therein. As shown in FIG. 1, the sensors 36 can be interspersed with the ultraviolet light emitting sources 30 about the receptacles. For example, in one embodiment, the sensors 36 can be formed on the inner wall surfaces 28 of the receptacles 22. The sensors 36 can be positioned in a variety of locations about the receptacles. These positions can include the whole depth of the receptacles 22, or limited regions (e.g., a central portion, a bottom portion and/or a top portion). The number and the type of sensors 36 that are deployed with the food handling instrument ultraviolet illuminator can vary and will generally depend on the type of treatment that is desired and the type of food handling instruments that are subject to be irradiated. In one embodiment, sensors 36 can be encapsulated in a module of ultraviolet light emitting sources 30 that are formed on the inner wall surfaces 28 of the receptacles 22. It is understood that the sensors 36 are not limited to being positioned within the receptacles. For example, the sensors 36 can be positioned in a variety of locations about the housing 20 (e.g., on the exterior wall surfaces 34 of the housing adjacent the openings 26).

The type of sensor 36 that can be deployed with the food handling instrument ultraviolet illuminators of the various embodiments can include a wide variety of sensors each configured to detect a number of different conditions. One or more of each of these sensors can be used singly or combination with any of the other different types of sensors. Examples of sensors that can be used with the food handling instrument ultraviolet illuminators of any of the various embodiments can include, but are not limited to, a fluorescent sensor, a presence sensor, an ultraviolet radiation sensor, a visible sensor (e.g., a visible camera), a proximity sensor, and environmental sensors. A fluorescent sensor (e.g., a fluorometer) can be configured to detect the fluorescent response generated from the surface of a food handling instrument and generate a fluorescent signal representative of the intensity of the fluorescence in the fluorescent response. A presence sensor can be located about each of the receptacles. In this manner, each presence sensor can detect the presence of a food handling instrument in a corresponding receptacle. The ultraviolet radiation sensor can detect the ultraviolet intensity that is in proximity of a food handling instrument in a receptacle after being irradiated with ultraviolet radiation from the ultraviolet light emitting source 30. A visible sensor such as a visible camera can obtain images from surfaces of a food handling instrument placed in a receptacle. A proximity sensor can detect the presence of a moving body that comes within the vicinity of the food handling instrument ultraviolet illuminators including the ultraviolet light emitting sources and/or the receptacles. The environmental sensors, which can include, but are not limited to, a humidity sensor, a temperature sensor, and a contamination sensor, can detect environmental conditions such as humidity, temperature, and a presence of contaminants, respectively.

The food handling instrument ultraviolet illuminators of the various embodiments can further include a control unit 38 that is coupled to the ultraviolet light emitting sources 30 and the sensors 36. As shown in FIG. 1, the control unit 38 can be placed on the exterior wall surfaces 34 of the housing 20. FIG. 1 shows the control unit 38 is placed on a narrow side surface 40 of the housing 20, however, it is understood that the control unit can be placed in a number of different positions. Regardless of position, the control unit 38 is configured to manage the irradiation of the plurality of receptacles 22 and any food handling instruments in the receptacles with the ultraviolet light emitting sources 30 as a function of the operational conditions detected by the one or more sensors 36. In this manner, the ultraviolet light emitting sources 30, the control unit 38 and the sensors 36 enable the food handling instrument ultraviolet illuminator of the various embodiments to incorporate a feedback mechanism that facilitates monitoring the irradiation of the food handling instruments. For example, this feedback mechanism enables the control unit 38 to determine a presence of harmful contaminants about the food handling instruments based on the conditions detected by the sensor(s). This allows the control unit 38 to direct the ultraviolet light emitting sources 30 to irradiate the food handling instruments at locations where there is a presence of harmful contaminants for removal and suppression thereof.

While directing the ultraviolet light emitting sources 30 to irradiate the food handling instruments, the control unit 38 can control the intensity and the duration of the irradiation by the ultraviolet light emitting sources 30 to effectuate an appropriate treatment of the instruments. The control unit 38 can also control other irradiation parameters including, but not limited to, the wavelength of the ultraviolet radiation emitted by the sources, the overall dosage of the ultraviolet radiation delivered to a surface of a food handling instrument by the sources, a power setting for operating the sources, and a maximum operating temperature of the sources. As explained below in more detail with respect to other embodiments, the control unit 38 can specify and change the irradiation parameters based on operational data obtained from one or more sensors.

In an embodiment in which a fluorescent sensor is utilized with a receptacle 22 to detect the fluorescent response generated from the surface of a food handling instrument placed therein, the control unit 38 can be configured to determine whether the intensity of the fluorescent signal detected by the fluorescent sensor is indicative of a contamination condition present on the surface of the food handling instrument. In this manner, the control unit 38 can activate the plurality of ultraviolet light emitting sources 30 to perform a disinfection operation on the surface of the food handling instrument in response to determining the contamination condition. In one embodiment, the control unit 38 can activate UV-C light emitting sources or blue-UV light emitting sources to perform the disinfection operation.

In one scenario, the control unit 38 can direct blue ultraviolet light emitting sources and/or UV-C light emitting sources to perform the disinfection operation depending on a level of extent of the contamination condition determined by the control unit. For example, the control unit 38 can direct a set of blue ultraviolet light emitting sources to continuously radiate the food handling instruments for a predetermined prolonged period of time to inhibit biological growth and a set of UV-C light emitting sources to radiate the instruments in a pulsed regime to reduce biological activity below a target level. For example, the time/duration of the UV-A exposure can range from ten minutes to tens of hours, while the time/duration of the UV-C exposure can be five minutes or less.

In another embodiment, the fluorescent sensor can be further configured to detect the intensity, the dosage, and the wavelength of the ultraviolet light that irradiates the food handling instruments placed in a receptacle. The control unit 38 can be configured to determine whether the intensity of the fluorescent signal detected by the fluorescent sensor is indicative of a contamination condition present on a surface of the food handling instruments. In this manner, the control unit 38 can activate one or more of the ultraviolet light emitting sources 30 that are configured to operate as an UV-C light emitting source and/or a blue ultraviolet light emitting source to perform a disinfection operation on the food handling instruments in response to determining the contamination condition.

In an embodiment in which a presence sensor is located about each of the receptacles 22 to detect the presence of a food handling instrument in a corresponding receptacle upon placement therein, the control unit 38 can be configured to direct the ultraviolet light emitting sources 30 to emit ultraviolet radiation towards any receptacle that recently received a food handling instrument upon receiving an indication thereof by a corresponding presence sensor. In one embodiment, the control unit can 38 be configured to direct the ultraviolet light emitting sources 30 to emit ultraviolet radiation towards any receptacle having a food handling instrument placed therein as determined by a corresponding presence sensor, regardless of when the instrument was inserted. In either scenario, the control unit 38 can be configured to control an intensity and a duration of the irradiation of the ultraviolet light that is directed towards the receptacle and food handling instruments held therein as a function of time that the food handling instruments are stored in the receptacle.

In an embodiment in which an ultraviolet radiation sensor is utilized to detect the ultraviolet intensity that is in proximity of a food handling instrument in a corresponding receptacle after being irradiated with ultraviolet radiation from the ultraviolet light emitting sources 30, the control unit 38 can be configured to adjust the intensity of the ultraviolet light emitting sources. In one embodiment, the control unit 38 can adjust the intensity of the ultraviolet light emitting sources 30 irradiating the receptacle and food handling instruments placed therein as a function of the intensity detected by the ultraviolet radiation sensors.

In one embodiment, an ultraviolet radiation sensor and a fluorescent sensor can be located about each of the plurality of receptacles. These sensors can operate in conjunction with multiple of sets of ultraviolet light emitting sources. For example, the ultraviolet radiation sensor can detect the ultraviolet intensity that is in proximity of a food handling instrument in a receptacle after being irradiated with ultraviolet radiation from a first set of ultraviolet light emitting sources, and the fluorescent sensor can detect the fluorescent illumination intensity excited from a surface of the food handling instrument after being irradiated by a second set of ultraviolet light emitting sources. In one embodiment, the control unit 38 can be configured to determine a density level of a target contaminant that is present on a surface of the food handling instrument. In this manner, the control unit 38 can activate one or more of the ultraviolet light emitting sources to direct ultraviolet light towards the surface of the food handling instrument in response to determining that the contaminant density level satisfies a predetermined threshold in order to eradicate the target contaminant.

In one embodiment in which a visible camera is utilized to obtain images from surfaces of a food handling instrument placed in a corresponding receptacle 22, the control unit 38 can be configured to determine a presence of contamination on the surfaces of the food handling instrument by comparing images obtained by the visible camera over different times. In this manner, the control unit 38 can direct the ultraviolet light emitting sources 30 to irradiate the food handling instrument where there is a presence of contamination for removal thereof and suppression of further growth. In addition, the control unit 38 can monitor the irradiation of the food handling instrument with the visible camera, and adjust irradiation parameters of the ultraviolet light emitting sources as a function of conditions detected by the visible camera.

In one embodiment, a fluorescent sensor and a visible camera can be located about each of the plurality of receptacles 22. In one scenario, the fluorescent sensor can detect the fluorescent illumination intensity excited from a surface of a food handling instrument after being irradiated by the ultraviolet light emitting sources 30 and the visible camera can obtain images of the fluorescent response generated from the surface of the food handling instrument. In one embodiment, the control unit can be configured to determine a presence of contamination on the surfaces of the food handling instrument by comparing images of the fluorescent response obtained by the visible camera over different times. To this extent, the control unit 38 can direct the ultraviolet light emitting sources 30 to irradiate the food handling instrument in response to determining a presence of contamination. In addition, the control unit can be configured to monitor the irradiation of the food handling instrument with the visible camera, and adjust irradiation parameters of the ultraviolet light emitting sources as a function of fluorescent response detected by the visible camera.

It is understood that the aforementioned examples of sensors that can be used to operate in conjunction with the control unit 38 with the food handling instrument ultraviolet illuminator of FIG. 1 as well as the other embodiments described herein are illustrative of a few options that can be used to control the irradiation of a food handling instrument, and are not meant to be limiting. Further, it is understood that this control of the irradiation in these other embodiments includes the control unit 38 monitoring the irradiation by the ultraviolet light emitting sources 30 and adjusting of any of the previously mentioned irradiation parameters based on feedback conditions detected by the sensors.

It is understood that the control unit 38 can control the operation of the ultraviolet light emitting sources 30 without the use of any sensors. In particular, the control unit 38 can activate the operation of the ultraviolet light emitting sources 30 in response to a user request received via a user input/output component 42. For example, the user input/output component 42 can be configured to have a variety of different treatment modes that a user can choose from. Each of these treatment modes can be configured to cause the ultraviolet light emitting sources 30 to irradiate the food handling instruments with radiation of certain wavelengths, intensities, dosages, patterns, distributions and the like that are designed to attain a predetermined type of treatment (e.g., a disinfection, sterilization, eradication of certain bacteria, viruses, parasitic agents, etc.).

The control unit 38 can direct the ultraviolet light emitting sources 30 to perform each of these treatments for a predetermined duration facilitated by the use of a timer that is part of the control unit or a separate component. In one embodiment, the control unit 38 operating in conjunction with the timer can manage the amount of time that the ultraviolet light emitting sources 30 radiate in the UV-C range versus the UV-B range and/or the blue ultraviolet range. For example, in FIG. 1, the control unit 38 operating in conjunction with the timer can manage the amount of time that the blue ultraviolet light emitting sources irradiate the food handling instruments with blue ultraviolet radiation, while the UV-C sources irradiate the instruments with UV-C radiation. The duration and frequency that these ultraviolet light emitting sources are utilized can be predetermined or can depend on detected condition signals provided to the control unit 38 by any of the sensors utilized to detect operational conditions. To this extent, the control unit 38 and the timer ensure that the ultraviolet light emitting sources 30 irradiate the food handling instruments for the predetermined duration so that a sufficient dosage is delivered.

As noted above, the control unit 38 can be configured to direct the ultraviolet light emitting sources 30 to irradiate food handling instruments that have been placed in the receptacles 22. The control unit 38 can control the intensity and the duration of the irradiation by the ultraviolet light emitting sources 30. In one embodiment, the control unit 38 can control the intensity and the duration of the irradiation as a function of time that the food handling instruments are stored in the receptacles 22. In one scenario, the control unit 38 can activate a set of UV-C light emitting sources after the timer measures that the food handling instruments have resided in the receptacles 22 for a predetermined time duration (e.g., multiple hours). In an embodiment, a user can instruct the control unit 38 to activate a set of UV-C light emitting sources when the food handling instrument is suspected of and/or known to include contaminants. After irradiation is complete, a notification can be provided to the user via a display, indicator, or the like that can operate in conjunction with the user input/output component 42. In this manner, the user, upon viewing such a display, can then be assured that the food handling instrument has been treated and is safe to use.

In general, the user input/output component 42 facilitates user interaction with the control unit 38 via a set of input buttons, touch screens, and/or the like 44, and at least one output button, screen, display, and/or the like 46, prior to initiating an ultraviolet irradiation treatment, during the treatment, and/or after the treatment. In this manner, the user can use any of the inputs 44 to specify various input selections regarding the irradiation parameters (e.g., intensity level, dosage, wavelength, irradiation pattern and duration) for controlling the irradiation of the food handling instruments in the receptacles with the ultraviolet light emitting sources 30. For example, after using one of the inputs 44 to activate an irradiation operation, the user can use the inputs to adjust one or more irradiation parameters associated with the ultraviolet light emitting sources 30 during a current treatment. In one embodiment, the user can use the inputs 44 to direct the control unit 38 to have the ultraviolet light emitting sources 30 automatically irradiate the receptacles 22 and food handling instruments placed therein at a set of predetermined times.

The output 46 part of the input/output component 42 can be configured to generate information to the user that is indicative of the irradiation of the food handling instruments in the receptacles 22 by the ultraviolet light emitting sources 30. The output can provide the information through one of a number of different modalities that include, but are not limited to, visual textual displays, visible indicator light displays (e.g., flashing lights), and auditory outputs generated by a speaker, and/or the like. For example, the output 46 can include a visual textual display that provides status information on the ultraviolet irradiation of the food handling instruments (e.g., time remaining, the presence of bacteria, viruses, germs, or the like) and the conditions of the instruments (e.g., surface changes, presence of contaminants). Other visual textual displays can include, but are not limited to, displaying information on one or more irradiation parameters that are associated with a current irradiation operation (e.g., radiative dose delivered to the food handling instruments), and displaying an indication of a date of the most recent irradiation treatment by the ultraviolet light emitting sources 30. Visible indicator light displays can be utilized to indicate a variety of conditions that include, but are not limited to, whether an ultraviolet irradiation treatment is recommended, whether the food handling instruments have been sterilized, disinfected, sanitized, whether an ultraviolet treatment is underway (e.g., an illuminated light), or whether the treatment is over (e.g., absence of an illuminated light).

The control unit 38 and the input/output component 42 can be placed about the food handling instrument ultraviolet illuminators described herein in one of a variety of locations. For example, as shown in FIG. 1, the control unit 38 and the input/output component 42 can be arranged about the exterior wall surfaces 34 of the housing 20 (e.g., side 40). Nevertheless, it is understood that the control unit 38 and the input/output component 42 can be arranged about the food handling instrument ultraviolet illuminators in other locations. Placement of these components will depend on the shape and the size of the food handling instrument ultraviolet illuminators as well as the type of instruments that are to be irradiated.

The control unit 38 can also include a number of different components that enable it to control the ultraviolet light emitting sources 30 and make determinations relating to the irradiation of the food handling instruments based on data obtained from the sensors 36. For example, in addition to the timer and user input/output component 42, the control unit 38 can include a memory storage that is capable of recording the various data obtained from the sensors. To this extent, the control unit 38 can retrieve the data for further analysis and optimization of the irradiation parameters of the ultraviolet light emitting sources 30.

The control unit 38 and/or the sensor(s) 36 can include a wireless transmitter and receiver that is configured to facilitate communications with each other at a remote location via WiFi, BLUETOOTH, and/or the like. As used herein, a remote location is a location that is apart from any of the food handling instrument ultraviolet illuminator described herein. For example, a remote computer can be used to transmit operational instructions to the wireless transmitter and receiver. The operational instructions can be used to program functions performed and managed by the control unit 38 and the sensors 36. In another embodiment, the wireless transmitter and receiver can transmit ultraviolet treatment results, data from and to the remote computer, to facilitate maintenance and diagnostic operations on the food handling instrument ultraviolet illuminators.

The food handling instrument ultraviolet illuminator 10 of FIG. 1 as well as the illuminators of the other embodiments can have a power component 48 that supplies power to the ultraviolet light emitting sources 30, the sensors 36, the control unit 38, the input/output component 42 and any other components (e.g., the timer) that rely on a power source to operate. The power component 48 can take the form of one or more of a variety of power sources. Examples of power sources that are suitable for use as the power component 48 can include, but are not limited to, one or more batteries (e.g., rechargeable batteries), a vibration power generator that can generate power based on magnetic inducted oscillations or stresses developed on a piezoelectric crystal, a rechargeable device such as a super capacitor.

These examples of power sources can be deployed in a number of locations about the food handling instrument ultraviolet illuminators. These types of power sources can be integrated with the housing 20 of the food handling instrument ultraviolet illuminators. For example, as shown in FIG. 1, the power component 48 can be placed on the exterior wall surfaces 34 of the housing 20. The use of the exterior wall surfaces 34 of the housing 20 to deploy the power sources is only one example, and thus, it is understood that these sources can be positioned in other locations about the food handling instrument ultraviolet illuminator. For example, a power source to the food handling instrument ultraviolet illuminators of the various embodiments can include a power station that is removably attachable with the housing. For example, the power station can include a stand with an insertable electrical contact that is removably attachable with the bottom portion of the housing of the food handling instrument ultraviolet illuminators.

The food handling instrument ultraviolet illuminators of the various embodiments can further include a heat dissipating component. To this extent, a heat dissipating component enables the electronic componentry associated with the ultraviolet light emitting sources 30, the sensors 36, the control unit 38, the input/output component 42, and other electrical components (e.g., the timer, the power sources) to operate efficiently without overheating. Examples of a heat dissipating component can include, but are not limited to, a heat sink, an air fan, and/or other heat dissipating mechanisms, such as liquid heating.

Figure 2:
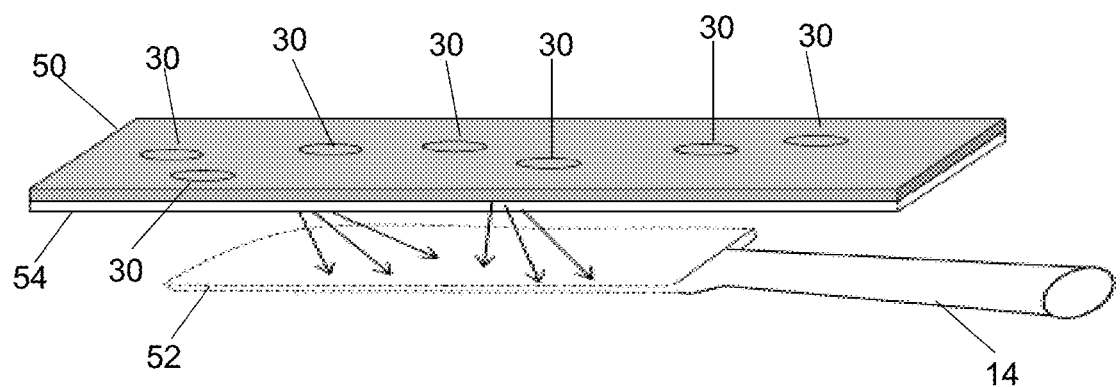
FIG. 2 shows a schematic of a light guiding layer operating in conjunction with a set of ultraviolet light emitting sources to irradiate a knife that is suited for deployment in the food handling instrument ultraviolet illuminator of FIG. 1 according to an embodiment.

A light guiding layer is one component that can be used with any of the food handling instrument ultraviolet illuminators described herein to enhance the irradiation of a food handling instrument. As used herein, a light guiding layer means a transparent material that is configured to guide ultraviolet light therein for transmission at one or more predetermined locations. FIG. 2 shows a schematic of a light guiding layer 50 operating in conjunction with a set of ultraviolet light emitting sources 30 to irradiate a blade 52 of a knife 14 that is suited for deployment in the food handling instrument ultraviolet illuminator 10 of FIG. 1 or the like. As shown in FIG. 2, the light guiding layer 50 can be optically coupled to the set of ultraviolet light emitting sources 30. Although not shown in FIG. 2, as well as FIG. 3 which shows an alternative light guiding layer embodiment, the light guiding layer 50 can be located about the inner wall surfaces of the receptacles. To this extent, the ultraviolet light emitted from the ultraviolet light emitting sources 30 can propagate through a region within the light guiding layer 50 before interacting with a surface of the blade 52 of the knife 14. This configuration enables the surfaces of the blade 52 of the knife 14 to be uniformly irradiated with ultraviolet light emitted from the ultraviolet light emitting sources, such that the distance between the knife 14 and the light guiding layer 50 does not change with time. Optionally, in one embodiment, as shown in FIG. 2, an ultraviolet transparent window 54, such as any of the types described above, can be used to transmit the ultraviolet light from the ultraviolet light emitting sources 30 and the light guiding layer 50 to the blade 52 of the knife 14.

Figure 3:
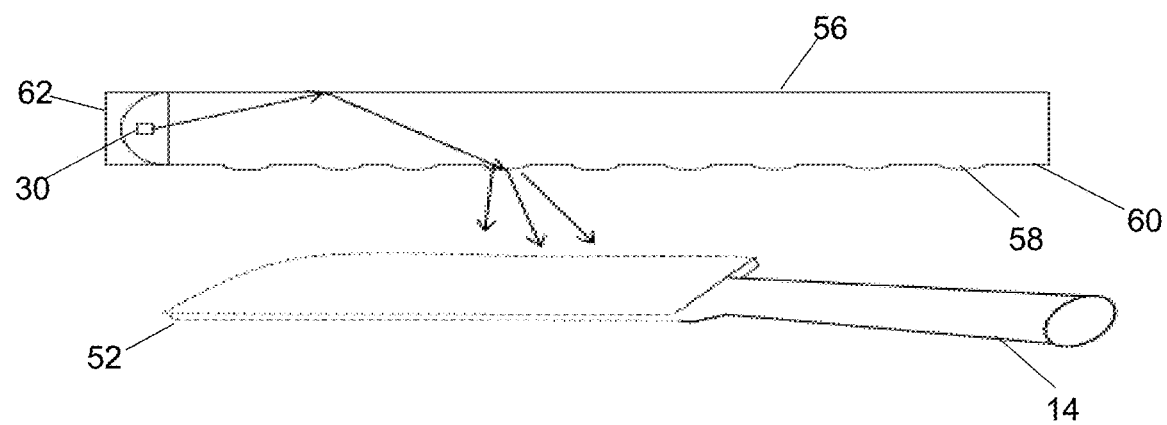
FIG. 3 shows a schematic of an alternative light guiding layer and ultraviolet light source configuration that is suited for deployment in the food handling instrument ultraviolet illuminator of FIG. 1 according to an embodiment.

In one embodiment, the light guiding layer 50 of FIG. 2, as well as the one depicted in FIG. 3, can comprise one or more ultraviolet transparent layers that have an index of refraction higher than ambient. The one or more ultraviolet transparent layers can include roughness domains that allow extraction of the ultraviolet light from the light guiding layer towards the surfaces of the blade 52 of the knife 14. In one embodiment, the one or more ultraviolet transparent layers can include diffusive domains that provide diffusive emission of the ultraviolet light from the light guiding layer to the surfaces of the blade 52 of the knife 14. The one or more ultraviolet transparent layers can comprise any of a variety of materials, including but not limited to a fluoropolymer and glass.

In one embodiment, the light guiding layers described herein can comprise scattering elements that interact with the light propagating through the light guiding layers and redirect the light toward the blade 52 of the knife 14. It is understood that the light guiding layers can comprise other types of ultraviolet transparent wave guiding material including, but not limited to, an ultraviolet fiber, a diffusive ultraviolet emitter, and/or the like.

As noted above, the light guiding layer can be configured with roughness domains that allow extraction of the ultraviolet light from the light guiding layer towards the surfaces of the blade 52 of the knife 14. FIG. 3 shows a schematic of an alternative light guiding layer and ultraviolet light source configuration that is suited for deployment in any of the food handling instrument ultraviolet illuminators described herein (e.g., the food handling instrument ultraviolet illuminator 10 of FIG. 1). In particular, FIG. 3 shows a light guiding layer 56 having a set of roughness domains 58 on a bottom portion 60 of the layer that directs the ultraviolet light generated from an ultraviolet light emitting source 30 positioned about a side portion 62 of the layer. In one embodiment, the ultraviolet light emitting source 30 can adhere to the side portion 62 of the light guiding layer 56 by an adhesive ultraviolet transparent material such as a fluoropolymer.

In operation, the ultraviolet light emitted from the ultraviolet light emitting source 30 can propagate through the light guiding layer 56 and be extracted from the bottom portion 60 of the layer via the roughness domains 58 to interact with a surface of the blade 52 of the knife 14. In one embodiment, the bottom portion 60 of the light guiding layer 56 including the roughness domains 58 can have a diffusive covering material in the form of a film or a layer that is configured to diffuse ultraviolet light generated from the ultraviolet light emitting source 30 towards the blade 52 of the knife 14. In one embodiment, the diffusive covering material can include, but is not limited to, a fluoropolymer.

The ultraviolet illuminators of the various embodiments can be configured with other components that can enhance the irradiation of any food handling instruments placed in any of the receptacles, compartments, racks, bins, holders, and the like, that are used to store and receive food handling instruments. In particular, the ultraviolet illuminators of the various embodiments can utilize a reflective layer to reflect the ultraviolet light generated from the ultraviolet light emitting sources 30. Having a reflective layer is beneficial in that it can facilitate and/or improve ultraviolet transmission, as well as promote recycling and light guiding of the radiation emitted from the sources 30. In general, a layer, film or coating of ultraviolet reflective material with a reflection coefficient of at least 50% will enable recycling of the ultraviolet radiation generated from the ultraviolet light emitting sources 30.

For example, in the embodiment depicted in FIG. 1, in which the kitchen illuminator 10 is used to irradiate a set of knives 14 and accompanying implements 16, a reflective layer or material can be applied to the inner wall surfaces 28 of the receptacles 22. The reflective layer or reflective material can cover all of the inner wall surfaces 28 or only limited regions. In one embodiment, the inner wall surfaces 28 of the receptacles 22 can have at least one reflective layer to reflect the ultraviolet light generated from the ultraviolet light emitting sources 30. The at least one reflective layer can include a fluoropolymer layer or an aluminum layer. In one embodiment, the at least one reflective layer can include UV-A or UV-C reflective material.

The reflective layer can include a number of different reflective materials. Examples of reflective material can include, but are not limited to, polished aluminum, $SiO_2$, $Al_2O_3$, PTFE (e.g., Teflon®), expanding polytetrafluoroethylene (ePTFE), ETFE or combinations thereof. In another embodiment, the reflective layer can include a diffusive ultraviolet reflective surface. In another embodiment, a transparent diffusive surface can be utilized. These types of surfaces can include a coating or thin film of a fluoropolymer. Examples of a fluoropolymer that enables these applications can include, but are not limited to, expanding polytetrafluoroethylene (ePTFE) membrane (e.g., GORE® DRP® Diffuse Reflector Material), polytetrafluoroethylene (PTFE), and/or the like.

Examples of ultraviolet reflective, diffusive ultraviolet, and transparent diffusive material that are suitable for use as a layer, film or coating can include, but are not limited to, polished aluminum, Bragg reflective dielectric mirrors, omni-directional mirrors comprising dielectric and metallic layers (e.g., aluminum), $SiO_2$, $Al_2O_3$, and/or the like. In one embodiment, ultraviolet reflective material such as a diffusive ultraviolet reflective material can be utilized to reflect the ultraviolet light generated from the ultraviolet light emitting sources 30 specularly or diffusively. A fluoropolymer is one example of material that is suitable as a diffusive ultraviolet reflective material that enables diffusive reflectivity. Such fluoropolymers can include, but are not limited to, expanding polytetrafluoroethylene (ePTFE) membrane (e.g., GORE® DRP® Diffuse Reflector Material), polytetrafluoroethylene (PTFE), and/or the like.

An optical element is another component that can be used with any of the food handling instrument ultraviolet illuminators of the various embodiments to enhance the irradiation of food handling instruments. In particular, the food handling instrument ultraviolet illuminators of the various embodiments can utilize one or more optical element to distribute the ultraviolet light emitted from the ultraviolet light emitting sources 30 about the food handling instruments. To this extent, the optical element can facilitate the irradiation of the food handling instruments for purposes of sterilization, disinfection, cleaning and/or treating for eradicating harmful bacteria, viruses, germs, parasitic agents, microorganisms, pathogens, contaminants and the like. For example, the optical element can be used to direct ultraviolet light generated from the ultraviolet light emitting sources 30 to food handling instruments placed in any of the receptacles, compartments, racks, bins, holders, and the like that are part of the food handling instrument ultraviolet illuminators that store and receive food handling instruments. In this manner, the optical element can ensure that surfaces of the food handling instruments requiring treatment are illuminated at a target intensity distribution.

Examples of optical elements that are suitable for use with any of the food handling instrument ultraviolet illuminators of the various embodiments include, but are not limited to, a mirror, a reflector, a lens (e.g., a Fresnel lens and a total internal reflection (TIR)) lens, ultraviolet transparent wave guiding material, scattering elements, or a diffusive element. In one embodiment, a lens element formed from a fluoropolymer material that includes, but is not limited to, $SiO_2$, $CaF_2$, $MgF_2$, or a fluoropolymer can be located about the ultraviolet light emitting sources 30. In one embodiment, in which the ultraviolet light emitting sources 30 include blue UV light emitting sources and UV-C light emitting sources, the sources can have a diffusive layer positioned above the light emitting faces of the blue UV light emitting sources and/or the UV-C light emitting sources.

Figure 4:
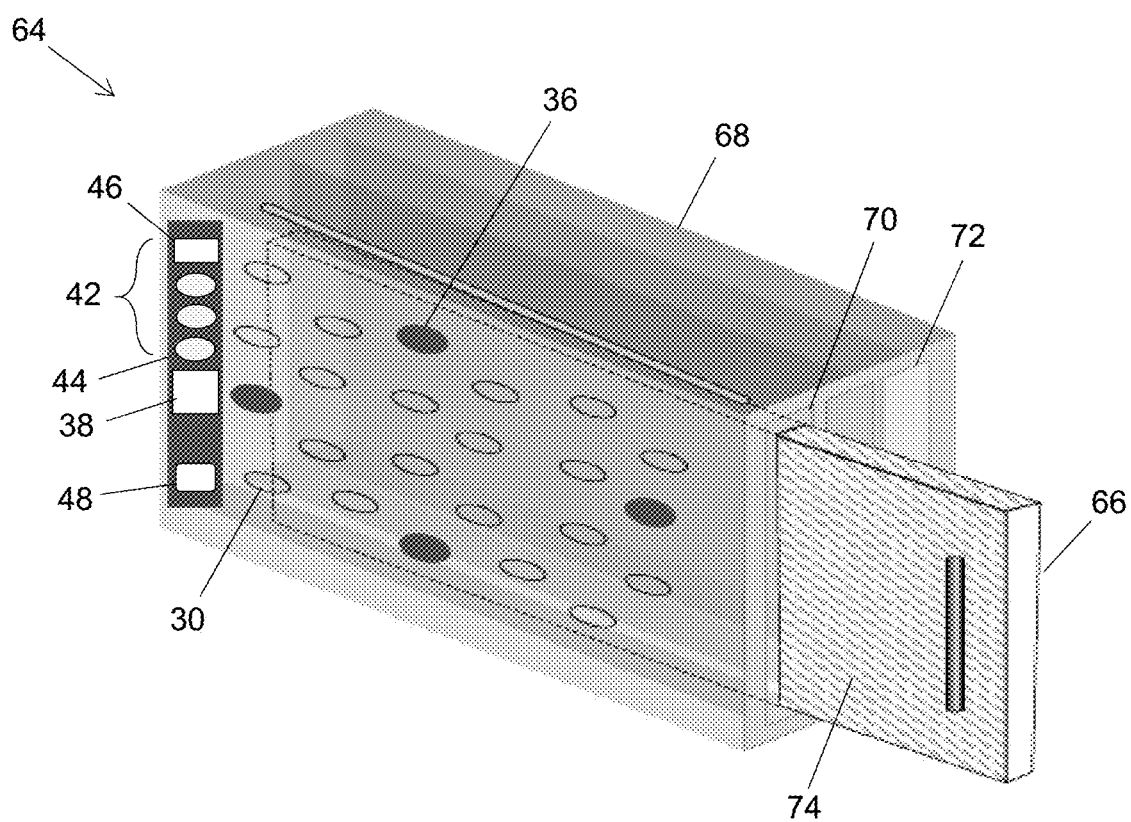
FIG. 4 shows a schematic of a food handling instrument ultraviolet illuminator for irradiating one or more cutting boards according to an embodiment.

The embodiments described with respect to FIGS. 1-3 are directed to irradiating food handling instruments such as knives and/or other cutlery items, however as noted above, the food handling instrument ultraviolet illuminator of the various embodiments can be utilized with other types of food handling instruments. For example, FIG. 4 shows a schematic of a food handling instrument ultraviolet illuminator 64 for irradiating one or more cutting boards 66 according to an embodiment. As shown in FIG. 4, the food handling instrument ultraviolet illuminator 64 includes a housing 68 with receptacles 70 formed in openings 72 that extend into an internal volume of the housing. In one embodiment, the receptacles 70 can take form of compartments that are configured to receive a cutting board 66. In one embodiment, the compartments can comprise a supporting frame that is configured to receive a cutting board 66. The supporting frame can secure the cutting board in the compartment maintaining a predetermined separation distance with the inner wall surfaces of the compartment. In one embodiment, the supporting frame can include a moveable frame that moves from an inserted position in which the cutting board is positioned within the housing 68 to a retracted position in which the cutting board 66 is moved to an exterior position that extends the cutting board out of the housing.

Although the compartments are depicted in FIG. 4 as having the same size (i.e., occupying the same volume of space in the housing 68), it is understood that the compartments can be configured to have different sizes in order to receive food handling instruments that vary by at least one of size, shape or function. For example, some of the compartments can be configured to receive cutting boards, while other compartments can be configured to received other food handling instruments including, but not limited to, knives and other cutlery items, food trays, dishware, etc.

Each of the receptacles 70 in the housing 68 of the food handling instrument ultraviolet illuminator 64 can be implemented with one or more of the previously mentioned components. For example, as shown in FIG. 4, the receptacles 70 can have ultraviolet light emitting sources 30 to direct ultraviolet light to a surface 74 of the cutting board 66. The ultraviolet light emitting sources 30 can be placed on the inner wall surfaces of each of the receptacles 70 in one of a variety of positions. For example, the ultraviolet light emitting sources 30 can be placed throughout the whole length of the inner wall surfaces or a limited region. In addition, the ultraviolet light emitting sources 30 can be placed on only one side of the inner wall surfaces of the receptacles 70. In this manner, the side of the cutting boards 66 that functions as the food preparation surface can be inserted into the receptacles such that it faces the ultraviolet light emitting sources. In one embodiment, the ultraviolet light emitting sources 30 can be placed on both sides of the inner wall surfaces of the receptacles 70, so that the sources can irradiate front and back surfaces of the cutting boards 66. In addition, ultraviolet light emitting sources 30 can also be placed at the bottom portion of the receptacles 70 (i.e., the part that receives an end region of the cutting boards 66). It is understood that the ultraviolet light emitting sources 30 that are utilized with the food handling instrument ultraviolet illuminator 64 can include any of the aforementioned types of sources (e.g., UV-B, UV-C and blue ultraviolet light emitting sources) used in one of a variety of arrangements.

FIG. 4 also shows that the food handling instrument ultraviolet illuminator 64 can utilize one or more sensors 36 to detect operational conditions associated with the receptacles 70 and any cutting boards 66 placed therein. Like other embodiments described herein, the sensors 36 can be interspersed with the ultraviolet light emitting sources 30 about the receptacles 70. The sensors that are utilized with the food handling instrument ultraviolet illuminator 64 can include any of the aforementioned sensors, whether used singly or in combination. In one embodiment, the sensors 36 can be used to detect contamination levels on front and back surfaces of the cutting board 66. For example, fluorescent sensors, visible sensors, and ultraviolet radiation sensors can be used individually or in combinations to detect contamination levels on front and back surfaces of the cutting board 66.

The food handling instrument ultraviolet illuminator 64 can also include a control unit 38 to manage the irradiation of the receptacles 70 and any cutting boards 66 placed in the receptacles with the ultraviolet light emitting sources 30. As discussed herein, the control unit 38 with or without the use of the user input/output component 42 and its input buttons 44 and output 46 can be used to manage the irradiation of the receptacles 70 and the cutting boards 66. As discussed herein, the control unit 38 can manage the ultraviolet light emitting sources 30 in one of a variety of approaches of which can depend on the types of sensors that are utilized to detect conditions about the receptacles 70 and the cutting boards 66.

All of the previously described approaches for irradiating food handling instruments and controlling the irradiation by the control unit 38 are suitable for use with the food handling instrument ultraviolet illuminator 64, as well as the illuminators of the other embodiments. For example, the control unit 38 can receive signals representative of contamination levels at a surface of a cutting board 66 that is in a receptacle 70 as detected by one or more of the sensors 36. In one embodiment, the control unit 38 can direct the ultraviolet light emitting sources 30 to irradiate surfaces of a cutting board 66 that has contamination levels that satisfy a predetermined contamination level that warrants an irradiation treatment. The control unit 38 can also monitor the irradiation of the cutting board 66 during the irradiation and adjust the intensity, dosage, and duration of any of the ultraviolet light emitting sources 30 as a function of the contamination levels detected by the sensors and/or the amount ultraviolet light that is detected at the surface of the cutting board. As noted above, the control unit 38 can be used to irradiate the cutting boards 66 in the receptacles 70 based on the time that the boards have been in the receptacles as detected by a presence sensor. Alternatively, the control unit 38 can direct the ultraviolet light emitting sources to irradiate the cutting boards based on a user making a request for such an action through the input buttons 44 of the input/output component 42. Information pertaining to the irradiation of the cutting boards 66 can be presented to a user through the output 46 of the input/output component 42.

The irradiation that is provided by the food handling instrument ultraviolet illuminator 64 as well as the other embodiments described below can be enhanced through the use of one or more of the aforementioned optical elements. For example, the food handling instrument ultraviolet illuminator 64 and the other illuminators can utilize items such as light guiding layers, reflective material, and/or optical elements to enhance the irradiation of the food handling instruments.

Figure 5:
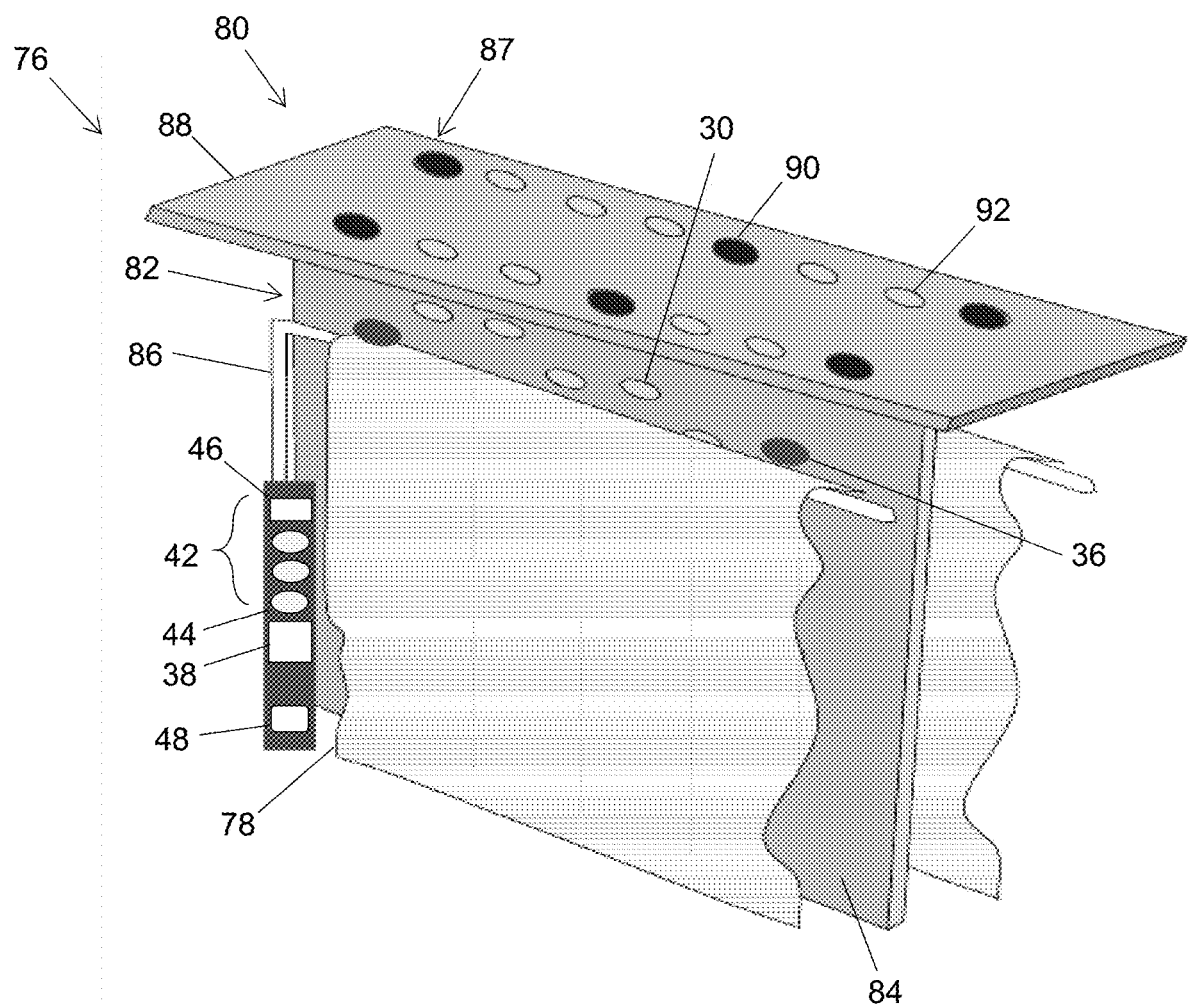
FIG. 5 shows a schematic of a food handling instrument ultraviolet illuminator for irradiating fabrics or textiles used in the preparation, cooking, eating and/or cleaning of food according to an embodiment.

FIG. 5 shows a schematic of a food handling instrument ultraviolet illuminator 76 for irradiating fabrics or textiles used in the preparation, cooking, eating and/or cleaning of food according to an embodiment. The food handling instrument ultraviolet illuminator 76 as depicted in FIG. 5, is directed to irradiating a kitchen towel such as a dish towel 78, however, it is understood that a wide variety of fabrics or textiles used in the preparation, cooking, eating and cleaning of food is suitable for use with this embodiment. Examples of such fabrics or textiles can include, but are not limited to, potholders, place mats and aprons.

The food handling instrument ultraviolet illuminator 76 of FIG. 5 can include a housing 80 with open-ended compartments 82 to receive one or more dish towels 78. As used herein, an open-ended compartment is a separate section of a structure (e.g., the housing 80) that is used to store, hold or retain an item (e.g., a dish towel 78) that is accessible or retrievable from a multiple of access points. The open-ended compartment 82 can include an inner wall surface 84 that separates the compartment from an adjoining compartment. In one embodiment, as shown in FIG. 5, the inner wall surface 84 of the open-ended compartment 82 can include a hanging bar 86 to retain a dish towel 78. Although the food handling instrument ultraviolet illuminator 76 of FIG. 5 is depicted with a hanging bar 86 it is understood that other types of storage or retention implements can be utilized with the inner wall surface 84 to hold the dish towel or other types of fabrics or textiles that are used or associated with eating and cooking. Examples of such implements can include, but are not limited to, hooks, retractable hanging lines, clips, tabs, etc.

The inner wall surface 84 of the open-ended compartments 82 can be implemented with one or more of the previously mentioned components. For example, the inner wall surface 84 of the open-ended compartments 82 can be further configured with ultraviolet light emitting sources 30 to direct ultraviolet light to the dish towel 78 and one or more sensors 36 to detect operational conditions associated with the dish towel. Although not shown in FIG. 5, the inner wall surface 84 of the open-ended compartments 82 can have other components interspersed with the ultraviolet light emitting sources 30 and the sensors 36 that enhance the irradiation of the dish towel 78 such as but not limited to, a light guiding layer, a reflective layer and an optical element. The types and numbers of sources, sensors and other components that are used with the open-ended compartments 82, as well as their arrangement with respect to the inner wall surface 84, the housing 80 and/or the dish towel 78 can vary, and also can take the form of one of the previously described embodiments.

The food handling instrument ultraviolet illuminator 76 can include a heating and air circulation unit 87 positioned about the open-ended compartments 82 to direct heated air and/or cooled air towards the hanging bar 86 and any dish towels 78 held by the bar. In one embodiment, as shown in FIG. 5, the heating and air circulation unit 87 can be located on a top region 88 of the housing 80 such that it extends over each of the open-ended compartments 82 formed in the housing. In this manner, heating elements 90 and cooling elements 92 that comprise the heating and air circulation unit 87 can direct heated air and cooling air, respectively, to the hanging bar 86 and any dish towels 78 held by the bar. To this extent, the heating elements 90 and the cooling elements 92 of the heating and air circulation unit 87 can be utilized to remove moisture from the dish towels 78 prior to, during, or after irradiation by the ultraviolet light emitting sources 30.

It is understood that the arrangement of the ultraviolet light emitting sources 30, the sensors 36 and the heating and air circulation unit 87 represents only one possible configuration and is not meant to be limiting. Those skilled in the art will appreciate that the ultraviolet light emitting sources 30, the sensors 36 and the heating and air circulation unit 87 can be arranged in a number of ways. For example, the ultraviolet light emitting sources 30 can be interspersed with the heating elements 90 and the cooling elements 92 of the heating and air circulation unit 87. In this scenario, the ultraviolet light emitting sources 30 can be oriented to direct the ultraviolet light downward towards any dish towels 78 on the hanging bar 86, enabling the irradiation of multiple sides of the towels.

Like other embodiments described herein, the food handling instrument ultraviolet illuminator 76 can include a control unit 38 to manage the irradiation of any dish towels 78 held by the hanging bar 86. The control unit 38 with or without the use of the user input/output component 42 and its input buttons 44 and output 46 can be used to manage the irradiation of the dish towels. The control unit 38 can manage the ultraviolet light emitting sources 30 in one of a variety of approaches of which, as mentioned above, can depend on the types of sensors that are utilized to detect conditions about the open-ended compartments 82 and the dish towels 78. All of the previously described approaches for irradiating food handling instruments and controlling the irradiation by the control unit 38 are suitable for use with the food handling instrument ultraviolet illuminator 76.

For example, in addition to any of the previously mentioned sensors that can be used to measure the contamination of food handling instruments, the food handling instrument ultraviolet illuminator 76 can utilize any of the aforementioned environmental sensors to detect environmental conditions associated with the dish towels 78. In one embodiment, a humidity sensor and/or a temperature sensor can be used to obtain data pertaining to the humidity, moisture; and temperature of the dish towels 78, respectively. Based on humidity, moisture and temperature data pertaining to the dish towels 78 as well as information relating to contamination levels, the control unit 38 can direct the ultraviolet light emitting sources to irradiate the towels. The control unit 38 can monitor the irradiation by adjusting the intensity, dosage and duration in manner that achieves disinfection or sterilization treatment and the like. It is understood that the control unit 38 can manage the irradiation of the dish towels 78 according to other scenarios using any of the aforementioned embodiments that utilize different types of sensors (e.g., fluorescent sensors, presence sensors, ultraviolet radiation sensors, etc.) Also, the control unit 38 can direct the ultraviolet light emitting sources 30 to irradiate the dish towels 78 based on a user making a request for such an action through the input buttons 44 of the input/output component 42.

Figure 6:
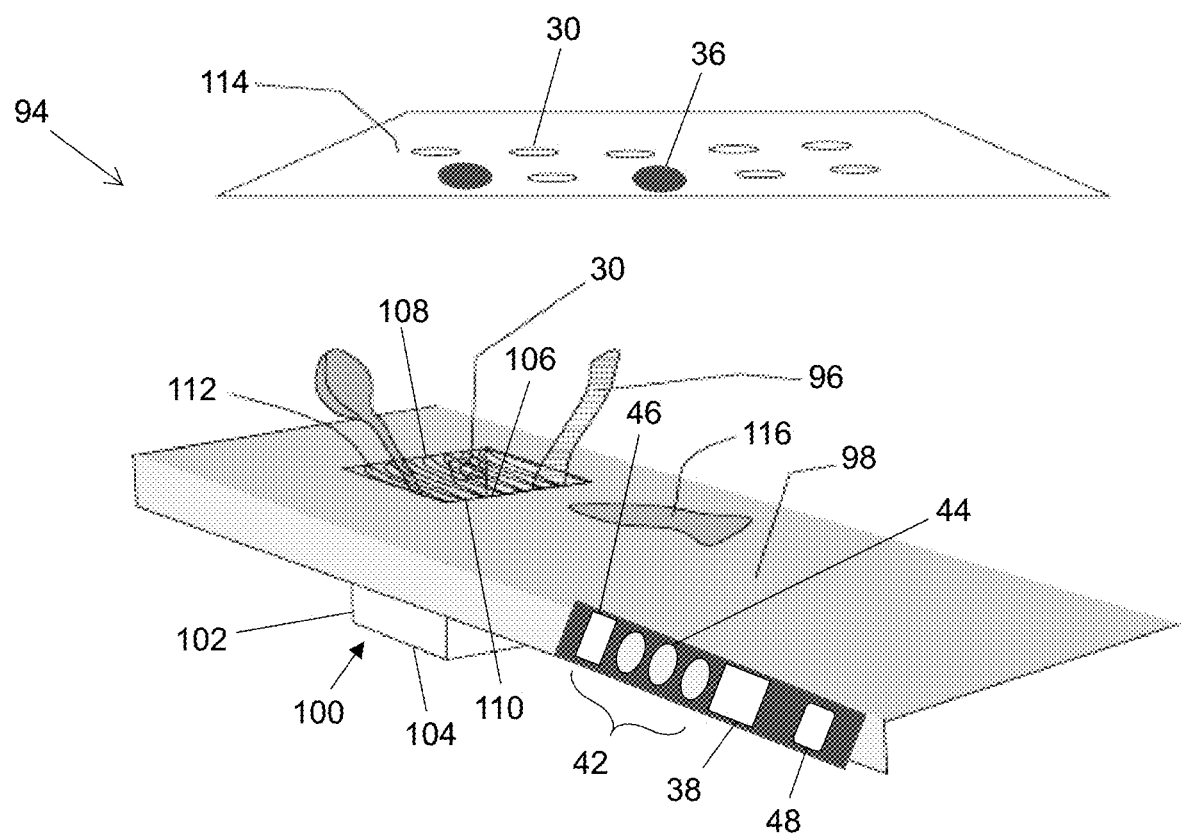
FIG. 6 shows a schematic of a food handling instrument ultraviolet illuminator for irradiating a multitude of different food handling instruments and nearby food preparation surfaces according to an embodiment.

FIG. 6 shows a schematic of a food handling instrument ultraviolet illuminator 94 for irradiating a multitude of different food handling instruments 96 and nearby food preparation surfaces 98 (e.g., a table, a food counter). The food handling instrument ultraviolet illuminator 94 can include a housing 100 to hold, retain, store, etc., one or more food handling instruments 96. The food handling instruments 96 can include any of a number of different utensils. The utensils can include, but are not limited to, knives, cooking or kitchen utensils (e.g., oversized forks and spoons, spatulas, tongs, presses, etc.), eating utensils, cutlery, and the like. In one embodiment, as shown in FIG. 6, the housing 100 can take the form of an enclosure 102 that is closed-ended on a bottom portion 104 and open-ended at a top portion 106 with an opening 108 to receive the food handling instruments 96. A covering 110 having a set of slits 112 can extend over all of the opening 108. The set of slits 112 facilitate placement of the food handling instruments 96 into the enclosure 102 and removal of the instruments from the enclosure. It is understood that the slits 112 can include openings, passages, cuts, entries, and the like that are configured to receive food handling instruments that can vary in size, shape and function.

One or more ultraviolet light emitting sources 30 can be located about the inner wall surfaces of the enclosure 102 in order to irradiate surfaces of the food handling instruments 96 that are positioned within the internal portion of the enclosure. The emitting faces of the ultraviolet light emitting source(s) 30 can be oriented in a variety of positions in order to irradiate the surfaces of the food handling instruments 96 at different positions, patterns, angular distributions, intensities, wavelengths, etc. Although not depicted in FIG. 6, it is understood that one or more sensors 36 can be placed about the internal portion of the enclosure 102 or near the top portion 106 to detect a variety of operation conditions before, during and after irradiation of the food handling instruments 96 by the ultraviolet light emitting source(s) 30.

The covering 110 can include one of a variety of materials. For example, the covering 110 can include an ultraviolet radiation absorbing material to prevent ultraviolet light from escaping from the enclosure 102 out through the opening 108 into the ambient. In one embodiment, the covering 110 can include an ultraviolet radiation absorbing material that is ultraviolet transparent to facilitate irradiation of the food handling instruments 96 from ultraviolet light emitting sources positioned external to the housing 100. In one embodiment, the covering 110 can include a reflective material of any of the aforementioned types that facilitate recycling of ultraviolet light. In addition, the covering 110 and/or the inner wall surfaces of the enclosure 102 can be configured with one or more of the previously described components that can enhance the irradiation of the food handling instruments 96 by the ultraviolet light emitting source(s) 30 including, but not limited to, a light guiding layer, a diffusive reflective layer, and an optical element.

As noted above, ultraviolet light emitting sources can be positioned external to the housing 100 in order to irradiate the food handling instruments 96 from another angle, in addition to, or in place of the ultraviolet light emitting source(s) 30 located about the internal portion of the enclosure 102. In one embodiment, FIG. 6 shows that the food handling instrument ultraviolet illuminator 94 can have an overhead disinfection unit 114 positioned over the top portion 106 of the enclosure 102 and the nearby food preparation surfaces 98. The overhead disinfection unit 114 can include a set of ultraviolet light emitting sources 30 that oriented downward to irradiate the food handling instruments 96 in the enclosure 102 including portions of the instruments that extend out from the covering 110 as well as portions of the instruments that are in the internal portion of the enclosure. In addition, the set of ultraviolet light emitting sources 30 associated with the overhead disinfection unit 114 can oriented to irradiate the nearby food preparation surfaces 98. The use of the overhead disinfection unit 114 makes the food handling instrument ultraviolet illuminator 94 well suited for commercial kitchen environments and even residential kitchen environments.

The types of ultraviolet light emitting sources 30 and the sensors 36 that are used with the housing 100 and the overhead disinfection unit 114 can include, but are not limited to, any of the types of sources and sensors previously mentioned. In addition, the ultraviolet light emitting sources 30 and the sensors 36 can be arranged to operate in conjunction with one another in a number of arrangements including, but are not limited to, any of the configuration discussed above.

In one embodiment, the food handling instrument ultraviolet illuminator 94 can utilize a proximity sensor that is configured to detect the presence of a moving body that comes within the vicinity of the ultraviolet light emitting sources 30 and/or the housing 100. The proximity sensor can be located with at least one of the enclosure 102, the overhead disinfection unit 114 or the nearby food preparation surfaces 98. To this extent, the ultraviolet light emitting sources 30 can be directed to not irradiate the food handling instruments 96 and/or the food preparation surfaces 98 if a moving body such as a person or an animal is determined to be in the proximity of the food handling instrument ultraviolet illuminator 94. For example, the control unit 38 can inactivate the ultraviolet light emitting sources 30 in either the enclosure 102 or the overhead disinfection unit 114, or maintain inactive sources in an inactive state in response to the proximity sensor detecting the presence of a moving body.

In one embodiment, the ultraviolet light emitting sources 30 of the overhead disinfection unit 114 can include at least one UV-C light emitting source configured to irradiate the surfaces of the food handling instruments 96 with a peak wavelength in an ultraviolet-UV-C disinfection range of 230 nm to 280 nm. In one embodiment, the ultraviolet light emitting sources 30 of the overhead disinfection unit 114 can further include at least one blue ultraviolet light emitting source configured to irradiate the food handling instruments 96 and/or the food preparation surfaces 98 with a peak wavelength in a blue ultraviolet light wavelength ranging from 360 nm to 460 nm. For example, the UV-C light emitting source(s) and the blue ultraviolet light emitting source(s) can perform a disinfection operation on the food handling instruments 96 and/or the food preparation surfaces 98. In one embodiment, the control unit 38 can direct the blue ultraviolet light emitting source(s) to continuously radiate the food handling instruments 96 and/or the food preparation surfaces 98 for a predetermined prolonged period of time to inhibit biological growth and the UV-C light emitting source(s) to radiate these items in a pulsed regime to reduce biological activity below a target level.

In one embodiment, the UV-C light emitting source(s) and the blue ultraviolet light emitting source(s) can be utilized along with selected sensors to identify regions of food handling instruments 96 in the enclosure 102 and/or the food preparation surfaces 98 that are contaminated. For example, blue ultraviolet light emitting source(s) in the overhead disinfection unit 114 can be configured to stimulate a fluorescent response from a surface of the food handling instruments 96 and/or the food preparation surfaces 98. For instance, the blue ultraviolet light emitting source(s) can irradiate the food handling instruments 96 and/or the food preparation surfaces 98 with fluorescent exiting radiation such as black light. The blue ultraviolet light emitting source(s) along with one or more UV-B light emitting sources can be used irradiate the food handling instruments 96 and/or the food preparation surfaces 98 with fluorescent exiting radiation. In one embodiment, a fluorescent sensor can be configured to detect the fluorescent response generated from the surface of the food handling instruments 96 and/or the food preparation surfaces 98 and generate a fluorescent signal representative of the intensity of the fluorescence in the fluorescent response. The control unit 38 can then determine whether the intensity of the fluorescent signal is indicative of a contamination condition present on the surface of the food handling instrument 96 and/or the food preparation surfaces 98. To this extent, the control unit 38 can activate at least one of the UV-C light emitting source(s) or the blue-UV light emitting source(s) to perform a disinfection operation on portions of the food handling instrument 96 and/or the food preparation surfaces 98 that are determined to have a contamination condition.

As an example, FIG. 6 shows a region 116 of the food preparation surfaces 98 that can be irradiated with fluorescent exiting radiation. The control unit 38 can then determine whether the intensity of the fluorescent signal generated from the region 116, as detected by a fluorescent sensor, is indicative of a contamination condition present on the food preparation surfaces 98. If the control unit 38 determines that the fluorescent signals are contaminated, then the control unit 38 can activate at least one of the UV-C light emitting source(s) or the blue-UV light emitting source(s) to perform a disinfection operation on region 116. It is understood that in this scenario, other types of sensors besides a fluorescent sensor can be used to determine contamination levels associated with the food handling instruments 96 and the food preparation surfaces 98. For example, as detailed above, a visible camera and an ultraviolet radiation sensor can be used with the ultraviolet light emitting sources 30 to determine contamination levels.

In one embodiment, a presence sensor can be located about the enclosure 102 and/or the overhead disinfection unit 114 to detect the presence of any food handling instruments placed in the enclosure. In this manner, the control unit 38 can direct the ultraviolet light emitting sources located about the internal portion of the enclosure 102 or the overhead disinfection unit 114 to emit ultraviolet radiation towards any food handling instruments 96 that have been recently placed in the enclosure in response to receiving an indication of the placement of the instruments by the presence sensor. In one embodiment, the control unit 38 can direct the ultraviolet light emitting sources to emit ultraviolet radiation towards the food handling instruments 96 after a predetermined time has elapsed since the presence sensor originally detected placement of the instruments in the enclosure 102. In one embodiment, the control unit 38 can control the intensity and the duration of the irradiation as a function of time that the food handling instruments 96 have been held in the enclosure 102.

In one embodiment, a user can utilize the user input/output component 42 to direct the control unit 38 to irradiate the food handling instruments 96 and/or the food preparation surfaces 98. As described previously, the inputs 44 and output 46 of the user input/output component 42 can be used to direct the ultraviolet light emitting sources 30 of the food handling instrument ultraviolet illuminator 94 to irradiate the food handling instruments 96 and/or the food preparation surfaces 98 in one of a number of approaches. For example, the user input/output component 42 can be used to direct the ultraviolet light emitting sources 30 of the overhead disinfection unit 114, via the control unit 38, to emit ultraviolet light towards the food handling instruments 96 and/or the food preparation surfaces 98 in instances when the kitchen space is not going to be in use over an extended period of time. In one embodiment, UV blue light emitting sources in the overhead disinfection unit 114 can be directed to radiate the kitchen space with prolonged or continuous UV blue radiation while the kitchen is not in use. Based on the inputs received from the user input/output component 42, the control unit 38 can select an appropriate ultraviolet light intensity level based on the duration of time that the kitchen space will not be in use. The duration, intensity and dose of radiation that the control unit 38 selects can be displayed to the user via output 46. If the user wants to make changes to these settings, he or she can then use the inputs 44 to override these settings and enter a customizable setting for at least one of the duration, intensity or dose of radiation.

Figure 7A:
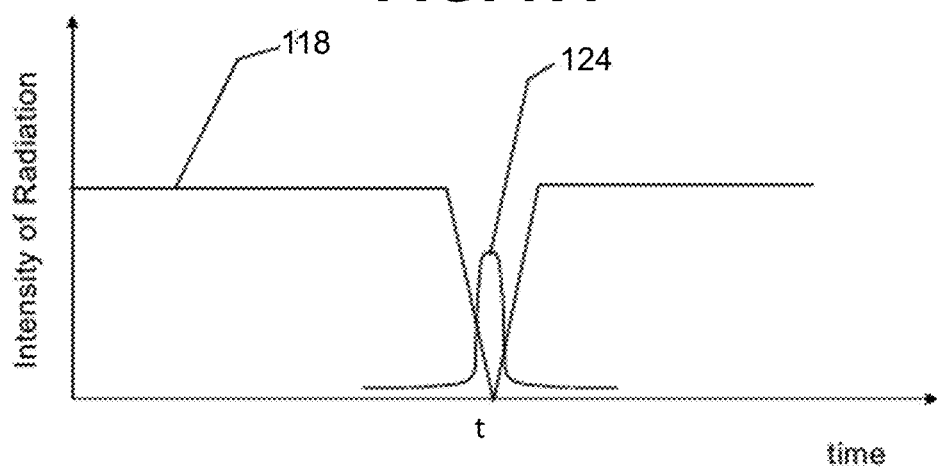
FIGS. 7A-7B show graphical examples depicting an ultraviolet irradiation treatment operation according to an embodiment of a food handling instrument that can be performed by any of the food handling instrument ultraviolet illuminators described herein.
Figure 7B:
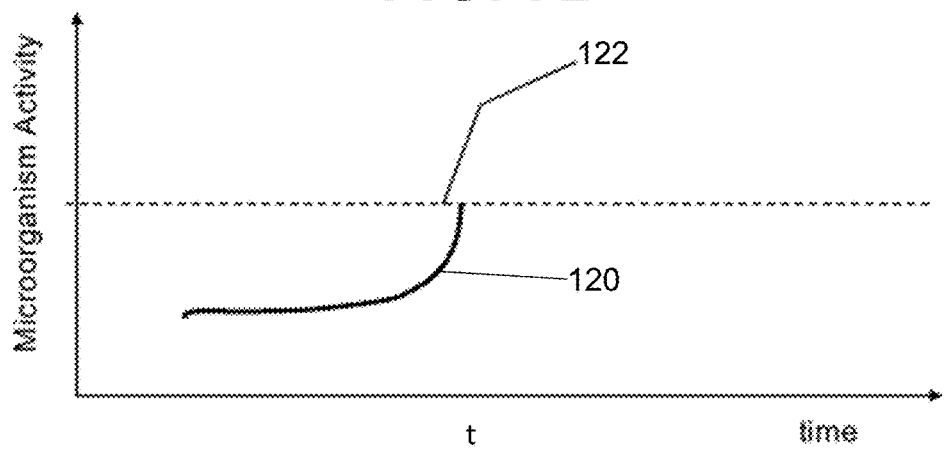

The food handling instrument ultraviolet illuminator of the various embodiments can be operated in a variety of manners to deliver an irradiation treatment to a food handling instrument. FIGS. 7A-7B show graphical examples depicting an ultraviolet irradiation treatment operation of a food handling instrument that can be performed by any of the food handling instrument ultraviolet illuminators described herein. As shown in FIG. 7A, at section 118 of the graph, ultraviolet radiation from a set of light emitting sources that emit light such as blue-UV radiation can be used to determine whether there is any contamination on a surface of the food handling instrument based on data from a sensor (e.g., an amplitude of a fluorescent signal sensed by a fluorescent sensor, visual data from a visual camera, and/or the like). For example, the food handling instrument can be irradiated with a light emitting source that is capable of eliciting a fluorescent signal if microbial activity is present. The amplitude of the fluorescent signal can indicate the level of contamination and/or the amount of microbial activity. The object can be irradiated by blue-UV radiation over a prolonged period of time that ranges from tens of minutes to tens of hours while determining whether there is a fluorescent signal. During this time, the control unit and the sensor (e.g., the fluorescence sensor, visual camera, and the like) can operate in conjunction to monitor the amount of contamination present on the surface of the object.

In this treatment, FIG. 7B shows a sharp increase in the growth of microorganism activity as noted by reference element 120. When the level of microorganism activity approaches a predetermined contamination threshold 122 at time t that is indicative of a need for more intense ultraviolet irradiation treatment due to rapid growth of microbial activity, then the control unit can direct a set of ultraviolet light emitting sources to emit UV-C radiation to perform a more intense ultraviolet irradiation treatment at a short burst of intensity that lasts at most a few minutes (FIG. 7A, reference number 124) starting at or shortly after time t. In this manner, ultraviolet radiation (e.g., UV-C radiation) applied from the set of ultraviolet light sources that deliver UV-C radiation can bring microbial activity within appropriate limits by rapidly suppressing microbial activity on the surface of the object. The blue-UV radiation from the set of light emitting sources that generate this type of radiation can be used to maintain microbial activity within limits over an extended period of time, while the UV-C radiation from the ultraviolet light sources that deliver UV-C radiation can be used to rapidly suppress microbial activity.

It is understood that the food handling instrument ultraviolet illuminators of the various embodiments as described herein can include other components that can complement the irradiation of food handling instruments in order to further enhance the sterilization, disinfection, treatment, and the like of these items. For example, the food handling instrument ultraviolet illuminators can utilize other sources to irradiate the items such as at least one visible light emitting source that emits visible light to the food handling instruments. To this extent, the visible light emitting source(s) can aid the ultraviolet light emitting source(s) in disinfecting any harmful contaminants from the food handling instruments and suppressing further growth of these contaminants. Examples of visible light sources that can be used include, but are not limited to, visible light emitting diodes, fluorescent radiation sources, fluorescent lights, compact fluorescent lights, neon lights, incandescent lights, etc. In one embodiment, a set of blue and visible light emitting diodes can be used with the ultraviolet radiation sources.

In one embodiment, a photocatalyst material can be used with any of the various embodiments to facilitate the irradiation of the food handling instruments in the receptacles. For example, the photocatalyst material can undergo a photocatalytic reaction in response to being irradiated by ultraviolet radiation. This photocatalytic reaction can facilitate the removal and suppression of any harmful contaminants present on the inner wall surfaces of the receptacles, compartments, etc., and/or the surfaces of any food handling instruments placed therein. The photocatalyst can include $TiO_2$, copper, silver and copper/silver particles, however, other photocatalysts such as, but not including, metal oxides, such as oxides of vanadium, chromium, titanium, zinc, tin, and cerium, can be used to enhance the sterilization and disinfection of the food handling instruments in a variety of applications.

In one embodiment, the photocatalyst can be irradiated by an ultraviolet wavelength in the presence of water vapor to result in formation of hydroxyl group radicals and reactive oxygen species (ROS) that can effectively interact and disrupt the proliferation of microorganisms. In an embodiment the ultraviolet wavelength can be in the range of 360 nm to 380 nm. In an alternative embodiment, the ultraviolet wavelength can be adjusted to be optimal for ROS and hydroxyl group radical formation for each type of photocatalyst used. It is understood that the photocatalyst should be positioned in proximity to the ultraviolet light to ensure that the created ROS and hydroxyl radicals can react with any harmful contaminants that may be present on the surface of food handling instrument.

In one embodiment, an ultraviolet active photocatalyst can be placed on the inner wall surfaces of the receptacles, compartments, etc. The ultraviolet active photocatalyst is configured to undergo a photocatalytic reaction in response to being irradiated by ultraviolet light generated from the ultraviolet light emitting sources 30 each operating at a peak wavelength. For example, the ultraviolet light emitting sources 30 can operate at a peak wavelength ranging 370 nm to 420 nm. To this extent, the photocatalytic reaction facilitates removal and suppression of any harmful contaminants present on the inner wall surfaces of the receptacles, compartments, etc.

Figure 8:
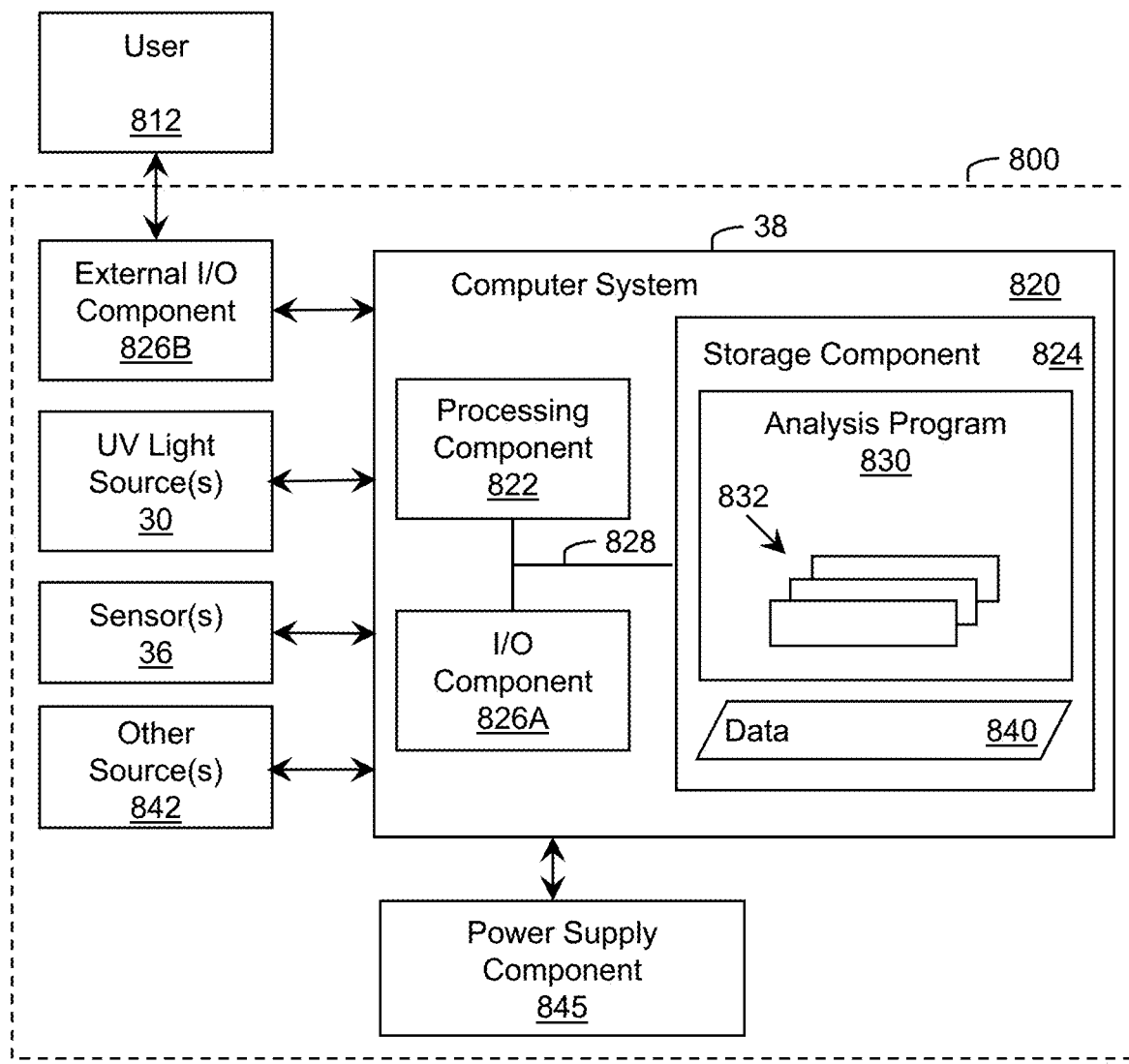
FIG. 8 shows a schematic block diagram representative of an overall processing architecture for irradiating a food handling instrument according to an embodiment that is applicable to any of the food handling instrument ultraviolet illuminators described herein.

FIG. 8 shows a schematic block diagram representative of an overall processing architecture of a system 800 for irradiating food handling instruments that is applicable to any of the food handling instrument ultraviolet illuminators described herein. In this embodiment, the architecture 800 is shown including the ultraviolet light emitting sources 30 and sensor(s) 36 for the purposes of illustrating the interaction of some of the components that can be used to provide an ultraviolet treatment.

As depicted in FIG. 8 and described herein, the system 800 can include a control unit 38. In one embodiment, the control unit 38 can be implemented as a computer system 820 including an analysis program 830, which makes the computer system 820 operable to manage the ultraviolet light emitting sources 30 and the sensor(s) 36 in the manner described herein. In particular, the analysis program 830 can enable the computer system 820 to operate the ultraviolet light emitting sources 30 to generate and deliver ultraviolet radiation and process data corresponding to one or more attributes regarding an irradiated item which can be acquired by the sensor(s) 36. The computer system 820 can individually control each ultraviolet light emitting source 30 and sensor 36 and/or control two or more of the ultraviolet light emitting sources and the sensors as a group. Furthermore, the ultraviolet light emitting sources 30 can emit ultraviolet radiation of substantially the same wavelength or of multiple distinct wavelengths, or at any other noted sets of peak wavelengths.

In an embodiment, during an initial period of operation, the computer system 820 can acquire data from at least one of the sensors 36 regarding one or more attributes of the item and generate data 840 for further processing. The data 840 can include information regarding a presence of biological activity (e.g., microorganisms, viruses, bacteria, and/or the like), an amount of radiation (e.g., ultraviolet, infrared, visible, and/or microwave) detected, and/or the like. The computer system 820 can use the data 840 to control one or more aspects of the ultraviolet radiation generated by the ultraviolet light emitting sources 30 during an ultraviolet treatment.

Furthermore, one or more aspects of the operation of the ultraviolet light emitting sources 30 can be controlled or adjusted by a user 812 via an external interface I/O component 826B. The external interface I/O component 826B can be located, for example, on the exterior of any of the aforementioned food handling instrument ultraviolet illuminators and used to allow the user 812 to selectively turn on/off the ultraviolet light emitting sources 30.

The external interface I/O component 826B can include, for example, a touch screen that can selectively display user interface controls, such as control dials, which can enable the user 812 to adjust one or more of: an intensity, scheduling, and/or other operational properties of the set of ultraviolet light emitting sources 30 or other sources (e.g., visible light emitting sources) 842 such as for example, operating parameters, radiation characteristics, and the like. In an embodiment, the external interface I/O component 826B could conceivably include a keyboard, a plurality of buttons, a joystick-like control mechanism, and/or the like, which can enable the user 812 to control one or more aspects of the operation of the set of ultraviolet light emitting sources 30. The external interface I/O component 826B also can include any combination of various output devices (e.g., an LED, a visual display), which can be operated by the computer system 820 to provide status information pertaining to a treatment for use by the user 812. For example, the external interface I/O component 826B can include one or more LEDs for emitting a visual light for the user 812, e.g., to indicate a status of the ultraviolet treatment. In an embodiment, the external interface I/O component 826B can include a speaker for providing an alarm (e.g., an auditory signal), e.g., for signaling that ultraviolet radiation is being generated or that an ultraviolet treatment has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors.

To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of a treatment. Illustrative aspects of the invention are further described in conjunction with the computer system 820. However, it is understood that the functionality described in conjunction therewith can be implemented by any type of monitoring and/or control system.

When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent computer systems that may perform a process described herein. To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 820 includes multiple computing devices, the computing devices can communicate over any type of communications link. Furthermore, while performing a process described herein, the computer system 820 can communicate with one or more other computer systems using any type of communications link. In either case, the communications link can comprise any combination of various types of wired and/or wireless links; any combination of one or more types of networks; and/or utilize any combination of various types of transmission techniques and protocols.

All of the components depicted in FIG. 8 can receive power from a power supply component 845. The power supply component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power supply component can include solar, a mechanical energy to electrical energy converter such as a piezoelectric crystal, a rechargeable device, a power station, etc.

While shown and described herein as a system and method, it is understood that aspects of the present invention further provide various alternative embodiments. For example, in one embodiment, the various embodiments of the present invention can include a computer program fixed in at least one computer-readable medium, which when executed, enables a computer system to facilitate the ultraviolet irradiation treatment. To this extent, the computer-readable medium includes program code, such as the analysis program 830, which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; and/or the like.

In another embodiment, the present invention can provide a method of providing a copy of program code, such as the analysis program 830, which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the present invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the various embodiments of the present invention can implement a method that facilitates an ultraviolet irradiation treatment. This can include configuring a computer system, such as the computer system 820, to implement a method for facilitating the ultraviolet treatment. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A food handling instrument ultraviolet illuminator, comprising:
    a housing having a plurality of receptacles each configured to receive one or more food handling instruments;
    a plurality of ultraviolet light emitting sources located about the plurality of receptacles to direct ultraviolet light towards the receptacles;
    one or more sensors located about the plurality of receptacles to detect operational conditions associated with the plurality of receptacles and any food handling instruments received therein, wherein the one or more sensors comprises a presence sensor located about each of the plurality of receptacles, each presence sensor configured to detect the presence of a food handling instrument in a corresponding receptacle; and
    a control unit, operatively coupled to the plurality of ultraviolet light emitting sources and the one or more sensors, wherein the control unit is configured to manage the irradiation of the plurality of receptacles and any food handling instruments in the receptacles with the plurality of ultraviolet light emitting sources as a function of the operational conditions detected by the one or more sensors, wherein the control unit is configured to direct the plurality of ultraviolet light emitting sources to emit ultraviolet radiation towards any receptacle having a food handling instrument placed therein as detected by a corresponding presence sensor, wherein the control unit is configured to control an intensity and a duration of the ultraviolet light that is directed towards the receptacle and food handling instrument as a function of time that the food handling instrument is stored in the receptacle.

2. The food handling instrument ultraviolet illuminator of claim 1, wherein the one or more sensors further comprises an ultraviolet radiation sensor and a fluorescent sensor located about each of the plurality of receptacles, wherein the ultraviolet radiation sensor is configured to detect the ultraviolet intensity that is in proximity of a food handling instrument in a receptacle after being irradiated with ultraviolet light from a first set of ultraviolet light emitting sources, and the fluorescent sensor is configured to detect the fluorescent illumination intensity excited from a surface of the food handling instrument after being irradiated by a second set of ultraviolet light emitting sources.

3. The food handling instrument ultraviolet illuminator of claim 2, wherein the control unit is configured to determine a density level of a target contaminant that is present on a surface of the food handling instrument as a function of the ultraviolet intensity and the fluorescent illumination intensity, the control unit activating one or more of the plurality of ultraviolet light emitting sources to direct ultraviolet light towards the surface of the food handling instrument to eradicate the target contaminant in response to determining that the contaminant density level satisfies a predetermined threshold.

4. The food handling instrument ultraviolet illuminator of claim 1, wherein the one or more sensors further comprises a visible camera located about each of the plurality of receptacles, wherein the visible camera is configured to obtain images from surfaces of a food handling instrument placed in a corresponding receptacle, wherein the control unit is configured to determine a presence of contamination on the surfaces of the food handling instrument by comparing images obtained by the visible camera over different times, wherein the control unit is configured to direct the plurality of ultraviolet light emitting sources to irradiate the food handling instrument when there is a presence of contamination, and wherein the control unit is configured to monitor the irradiation of the food handling instrument with the visible camera, and adjust irradiation parameters of the ultraviolet light emitting sources as a function of conditions detected by the visible camera.

5. The food handling instrument ultraviolet illuminator of claim 4, wherein the one or more sensors further comprises a fluorescent sensor located about each of the plurality of receptacles, wherein the fluorescent sensor is configured to detect the fluorescent illumination intensity excited from a surface of the food handling instrument after being irradiated by the plurality of ultraviolet light emitting sources, and the visible camera is configured to obtain images of the fluorescent response generated from the surface of the food handling instrument, wherein the control unit is configured to determine a presence of contamination on the surfaces of the food handling instrument by comparing images of the fluorescent response obtained by the visible camera over different times, wherein the control unit is configured to direct the plurality of ultraviolet light emitting sources to irradiate the food handling instrument in response to determining a presence of contamination, and wherein the control unit is configured to monitor the irradiation of the food handling instrument with the visible camera, and adjust irradiation parameters of the ultraviolet light emitting sources as a function of fluorescent response detected by the visible camera.

6. The food handling instrument ultraviolet illuminator of claim 1, further comprising a power component that supplies power to the plurality of ultraviolet light emitting sources, the one or more sensors, and the control unit.

7. The food handling instrument ultraviolet illuminator of claim 1, further comprising an ultraviolet active photocatalyst on an inner wall surface of at least one of the receptacles, wherein the ultraviolet active photocatalyst is configured to undergo a photocatalytic reaction in response to being irradiated by ultraviolet light, the photocatalytic reaction facilitating removal and suppression of any harmful contaminants present on the inner wall surfaces of the at least one receptacle and/or any kitchen instruments placed therein.

8. A food handling instrument ultraviolet illuminator, comprising:
a housing having a plurality of receptacles each configured to receive one or more food handling instruments;
a plurality of ultraviolet light emitting sources located within each of the plurality of receptacles to direct ultraviolet light towards any food handling instruments placed within the receptacles, wherein the plurality of ultraviolet light emitting sources direct the ultraviolet light to multiple surfaces of the food handling instruments including front and back surfaces of the food handling instruments, wherein at least one of the plurality of ultraviolet light emitting sources is an ultraviolet-C (UV-C) light emitting source configured to irradiate the surfaces of the food handling instruments with a peak wavelength in an ultraviolet-C (UV-C) disinfection range of 230 nm to 280 nm, and wherein at least one of the plurality of ultraviolet light emitting sources is a blue ultraviolet light emitting source configured to irradiate the surfaces of the food handling instruments with a peak wavelength in a blue ultraviolet light wavelength ranging from 360 nm to 460 nm;
one or more sensors located about the plurality of receptacles to detect operational conditions associated with the plurality of receptacles and any food handling instruments received therein; and
a control unit, operatively coupled to the plurality of ultraviolet light emitting sources and the one or more sensors, wherein the control unit is configured to manage the irradiation of any food handling instruments in the receptacles with the plurality of ultraviolet light emitting sources as a function of the operational conditions detected by the one or more sensors, wherein the control unit is configured to activate the UV-C light emitting source and the blue ultraviolet light emitting source to perform a disinfection operation on a food handling instrument in response to determining a contamination condition based on operational conditions detected by the one or more sensors, wherein the control unit is configured to direct the blue ultraviolet light emitting source to continuously irradiate the food handling instrument with blue ultraviolet light in the peak blue ultraviolet light wavelength for a predetermined prolonged period of time to inhibit biological growth and direct the UV-C light emitting source to irradiate the food handling instrument with UV-C light in the peak UV-C wavelength in a pulsed regime to reduce biological activity below a target level.

9. The food handling instrument ultraviolet illuminator of claim 8, wherein the blue ultraviolet light emitting source is further configured to stimulate a fluorescent response from the surfaces of the food handling instruments.

10. The food handling instrument ultraviolet illuminator of claim 9, wherein the one or more sensors comprises a fluorescent sensor configured to detect the fluorescent response generated from the surfaces of the food handling instruments and generate a fluorescent signal representative of the intensity of the fluorescence in the fluorescent response.

11. The food handling instrument ultraviolet illuminator of claim 10, wherein the control unit is configured to determine whether the intensity of the fluorescent signal detected by the fluorescent sensor is indicative of a contamination condition present on any of the surfaces of the food handling instruments.

12. The food handling instrument ultraviolet illuminator of claim 8, further comprising a user input/output component configured to facilitate user interaction with the control unit to control the irradiation of the receptacles and any food handling instruments placed therein with the plurality of ultraviolet light emitting sources, wherein the user input/output component is configured to receive user input that is indicative of an adjustment to one or more irradiation parameters associated with the plurality of ultraviolet light emitting sources, and wherein the user input/output component is configured to generate information indicative of the irradiation of the receptacles and/or any food handling instruments placed therein by the plurality of ultraviolet light emitting sources.

13. A food handling instrument ultraviolet illuminator, comprising:
a housing having a plurality of compartments each configured to receive one or more food handling instruments that vary by at least one of size, shape or function, wherein the compartments vary by at least one of size, shape, or depth within the housing;
a plurality of ultraviolet light emitting sources located within each of the plurality of compartments to direct ultraviolet light towards any food handling instruments placed in the compartments, wherein at least one of the plurality of ultraviolet light emitting sources is an ultraviolet-C (UV-C) light emitting source configured to irradiate the surfaces of the food handling instruments with a peak wavelength in an ultraviolet-C (UV-C) disinfection of 230 nm to 280 nm;
one or more sensors located about the plurality of compartments to detect contamination levels on any food handling instruments received therein, wherein the one or more sensors comprises a fluorescent sensor and a visible camera located about each of the plurality of compartments, wherein the fluorescent sensor is configured to detect fluorescent illumination intensity excited from a surface of the food handling instruments after being irradiated by the plurality of ultraviolet light emitting sources, and the visible camera is configured to obtain images of the fluorescent response generated from the surface of the food handling instruments;

a control unit, operatively coupled to the plurality of ultraviolet light emitting sources and the one or more sensors, wherein the control unit is configured to direct the plurality of ultraviolet light emitting sources to irradiate surfaces of any food handling instruments deemed to have a presence of contamination, wherein the control unit is configured to determine that there is a presence of contamination by comparing images of the fluorescent response obtained by the visible camera over different times, and wherein the control unit is configured to monitor the irradiation of the food handling instruments with the visible camera and adjust irradiation parameters of any of the ultraviolet light emitting sources as a function of the fluorescent response detected by the visible camera; and a user input/output component configured to facilitate user interaction with the control unit to control the irradiation of the food handling instruments by the plurality of ultraviolet light emitting sources.

14. The food handling instrument ultraviolet illuminator of claim 13, further comprising a light guiding layer optically coupled to the plurality ultraviolet light emitting sources that are located within each of the plurality of compartments, wherein the ultraviolet light emitted from the plurality of ultraviolet light emitting sources propagates through a region within the light guiding layer before interacting with any inner wall surfaces of the compartments and/or any food handling instruments placed therein.

15. The food handling instrument ultraviolet illuminator of claim 14, wherein the light guiding layer comprises roughness domains that allow extraction of the ultraviolet light from the light guiding layer to the inner wall surfaces of the compartments and/or any food handling instruments placed therein.

16. The food handling instrument ultraviolet illuminator of claim 13, further comprising a set of overhead ultraviolet light emitting sources located over the plurality of compartments, wherein the set of overhead ultraviolet light emitting sources are oriented to direct ultraviolet light downward towards the plurality of compartments and surfaces that are in proximity to the compartments.

17. The food handling instrument ultraviolet illuminator of claim 16, wherein the one or more sensors comprises a proximity sensor that is configured to detect the presence of a moving body that comes within the vicinity of the set of overhead ultraviolet light emitting sources and/or the plurality of compartments, wherein the control unit is configured to inactivate the set of overhead ultraviolet light emitting sources or maintain inactive sources in an inactive state in response to the proximity sensor detecting the presence of a moving body.

18. The food handling instrument ultraviolet illuminator of claim 13, further comprising a heating and air circulation unit positioned about the plurality of receptacles, to direct heated air and/or cooled air towards the compartments and any food handling instruments placed therein.

19. The food handling instrument ultraviolet illuminator of claim 13, wherein the user input/output component is configured to receive user input that indicates an adjustment to one or more irradiation parameters associated with the plurality of ultraviolet light emitting sources, the irradiation parameters including intensity level, dosage, wavelength, irradiation pattern and duration.

20. The food handling instrument ultraviolet illuminator of claim 14, wherein the light guiding layer comprises one or more ultraviolet transparent layers, wherein the one or more ultraviolet transparent layers comprises diffusive emitting domains that diffusively emit ultraviolet light towards the food handling instruments.

\* \* \* \* \*